(12) United States Patent
Reches et al.

(10) Patent No.: US 11,925,724 B2
(45) Date of Patent: Mar. 12, 2024

(54) COMPOUNDS WITH DUAL ACTIVITY

(71) Applicant: Yissum Research Development Company of the Hebrew University of Jerusalem Ltd., Jerusalem (IL)

(72) Inventors: Meital Reches, Bet Hasmonai (IL); Sivan Yuran, Jerusalem (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 1212 days.

(21) Appl. No.: 15/758,479

(22) PCT Filed: Sep. 7, 2016

(86) PCT No.: PCT/IL2016/050989
§ 371 (c)(1),
(2) Date: Mar. 8, 2018

(87) PCT Pub. No.: WO2017/042805
PCT Pub. Date: Mar. 16, 2017

(65) Prior Publication Data
US 2018/0296727 A1    Oct. 18, 2018

Related U.S. Application Data

(60) Provisional application No. 62/215,278, filed on Sep. 8, 2015.

(51) Int. Cl.
| | |
|---|---|
| A61L 27/34 | (2006.01) |
| C07K 7/06 | (2006.01) |
| C08K 5/31 | (2006.01) |
| C09D 5/02 | (2006.01) |
| C09D 7/40 | (2018.01) |
| C09D 7/42 | (2018.01) |

(52) U.S. Cl.
CPC .............. *A61L 27/34* (2013.01); *C07K 7/06* (2013.01); *C09D 5/028* (2013.01); *C09D 7/42* (2018.01); *C09D 7/70* (2018.01); *A61L 2420/02* (2013.01); *A61L 2420/04* (2013.01); *C08K 5/31* (2013.01)

(58) Field of Classification Search
None
See application file for complete search history.

(56) References Cited

FOREIGN PATENT DOCUMENTS

WO    2014/118779 A1    8/2014

OTHER PUBLICATIONS

WebMD (https://www.webmd.com/beauty/what-is-breast-implant-illness accessed Jun. 12, 2023).*
Bumgardner et al., "Emerging Antibacterial Biomaterial Strategies for the Prevention of Peri-implant Inflammatory Diseases", The International Journal of Oral & Maxillofacial Implants, 2011, vol. 26, No. 3, pp. 553-560.
Noel et al., "Development of a Polyester Coating Combining Antithrombogenic and Cell Adhesive Properties: Influence of Sequence and Surface Density of Adhesion Peptides", Biomacromolecules, 2015, vol. 16, pp. 1682-1694.
Shin et al., "Biomimetic materials for tissue engineering", Biomaterials, 2003, vol. 24, pp. 4353-4364.
Subbiahdoss et al., "Bacterial Biofilm Formation Versus Mammalian Cell Growth on Titanium-Based Mono—and Bi-Functional Coatings", European Cells and Materials, 2010, vol. 19, pp. 205-213.
Tosatti et al., "Peptide functionalized poly(L-lysine)-g-poly(ethylene glycol) on titanium: resistance to protein adsorption in full heparinized human blood plasma", Biomaterials, 2003, vol. 24, pp. 4949-4958.

* cited by examiner

*Primary Examiner* — Julie Ha
*Assistant Examiner* — Tara L Martinez
(74) *Attorney, Agent, or Firm* — Vorys, Sater, Seymour and Pease LLP; Anthony P. Venturino

(57) ABSTRACT

Provided are novel compounds and uses thereof in preventing antifouling by unicellular organisms and in attracting cells from multicellular organisms.

39 Claims, 8 Drawing Sheets
Specification includes a Sequence Listing.

Peptide 1

Peptide 2

Peptide 3

Peptide 4

SEQUENCE LISTING

<160> NUMBER OF SEQ ID NOS: 18

<210> SEQ ID NO 1
<211> LENGTH: 4
<212> TYPE: PRT
<213> ORGANISM: Artificial Sequence
<220> FEATURE:
<223> OTHER INFORMATION: sequence promoting adherence of cells

<400> SEQUENCE: 1

Arg Gly Asp Ser
1

<210> SEQ ID NO 2
<211> LENGTH: 6
<212> TYPE: PRT
<213> ORGANISM: Artificial Sequence
<220> FEATURE:
<223> OTHER INFORMATION: sequence promoting adherence of cells

<400> SEQUENCE: 2

Lys Gln Ala Gly Asp Val
1               5

<210> SEQ ID NO 3
<211> LENGTH: 5
<212> TYPE: PRT
<213> ORGANISM: Artificial Sequence
<220> FEATURE:
<223> OTHER INFORMATION: sequence promoting adherence of cells

<400> SEQUENCE: 3

Tyr Ile Gly Ser Arg
1               5

<210> SEQ ID NO 4
<211> LENGTH: 4
<212> TYPE: PRT
<213> ORGANISM: Artificial Sequence
<220> FEATURE:
<223> OTHER INFORMATION: sequence promoting adherence of cells

<400> SEQUENCE: 4

Arg Glu Asp Val
1

<210> SEQ ID NO 5
<211> LENGTH: 5
<212> TYPE: PRT
<213> ORGANISM: Artificial Sequence
<220> FEATURE:
<223> OTHER INFORMATION: sequence promoting adherence of cells

<400> SEQUENCE: 5

Ile Lys Val Ala Val
1               5

<210> SEQ ID NO 6
<211> LENGTH: 10
<212> TYPE: PRT
<213> ORGANISM: Artificial Sequence
<220> FEATURE:
<223> OTHER INFORMATION: sequence promoting adherence of cells

<400> SEQUENCE: 6

Arg Asn Ile Ala Glu Ile Ile Lys Asp Ile
1               5                   10

<210> SEQ ID NO 7
<211> LENGTH: 10
<212> TYPE: PRT
<213> ORGANISM: Artificial Sequence
<220> FEATURE:
<223> OTHER INFORMATION: sequence promoting adherence of cells

<400> SEQUENCE: 7

Lys His Ile Phe Ser Asp Asp Ser Ser Glu
1               5                   10

<210> SEQ ID NO 8
<211> LENGTH: 5
<212> TYPE: PRT
<213> ORGANISM: Artificial Sequence
<220> FEATURE:
<223> OTHER INFORMATION: sequence promoting adherence of cells

<400> SEQUENCE: 8

Val Pro Gly Ile Gly
1               5

<210> SEQ ID NO 9
<211> LENGTH: 7
<212> TYPE: PRT
<213> ORGANISM: Artificial Sequence
<220> FEATURE:
<223> OTHER INFORMATION: sequence promoting adherence of cells

<400> SEQUENCE: 9

Phe His Arg Arg Ile Lys Ala
1               5

<210> SEQ ID NO 10
<211> LENGTH: 4
<212> TYPE: PRT
<213> ORGANISM: Artificial Sequence
<220> FEATURE:
<223> OTHER INFORMATION: sequence promoting adherence of cells

<400> SEQUENCE: 10

Lys Arg Ser Arg

```
<210> SEQ ID NO 11
<211> LENGTH: 21
<212> TYPE: PRT
<213> ORGANISM: Artificial Sequence
<220> FEATURE:
<223> OTHER INFORMATION: sequence promoting adherence of cells

<400> SEQUENCE: 11

Asn Ser Pro Val Asn Ser Lys Ile Pro Lys Ala Cys Cys Val Pro Thr
1               5                   10                  15

Glu Leu Ser Ala Ile
            20

<210> SEQ ID NO 12
<211> LENGTH: 4
<212> TYPE: PRT
<213> ORGANISM: Artificial Sequence
<220> FEATURE:
<223> OTHER INFORMATION: sequence promoting adherence of cells

<400> SEQUENCE: 12

Ala Pro Gly Leu
1

<210> SEQ ID NO 13
<211> LENGTH: 9
<212> TYPE: PRT
<213> ORGANISM: Artificial Sequence
<220> FEATURE:
<223> OTHER INFORMATION: sequence promoting adhesive of cells

<400> SEQUENCE: 13

Ala Ala Ala Ala Ala Ala Ala Ala Ala
1               5

<210> SEQ ID NO 14
<211> LENGTH: 6
<212> TYPE: PRT
<213> ORGANISM: Artificial Sequence
<220> FEATURE:
<223> OTHER INFORMATION: Peptide 1
<220> FEATURE:
<221> NAME/KEY: MOD_RES
<222> LOCATION: (1)..(1)
<223> OTHER INFORMATION: 3,4 dihydroxy variant of Phe
<220> FEATURE:
<221> NAME/KEY: MOD_RES
<222> LOCATION: (2)..(3)
<223> OTHER INFORMATION: 4F variant of Phe
<220> FEATURE:
<221> NAME/KEY: MOD_RES
<222> LOCATION: (6)..(6)
<223> OTHER INFORMATION: amidation of Asp

<400> SEQUENCE: 14

Phe Phe Phe Arg Gly Asp
1               5

<210> SEQ ID NO 15
<211> LENGTH: 6
<212> TYPE: PRT
<213> ORGANISM: Artificial Sequence
<220> FEATURE:
<223> OTHER INFORMATION: Peptide 2
<220> FEATURE:
<221> NAME/KEY: MOD_RES
<222> LOCATION: (1)..(2)
```

```
<223> OTHER INFORMATION: 4F variant of Phe
<220> FEATURE:
<221> NAME/KEY: MOD_RES
<222> LOCATION: (3)..(3)
<223> OTHER INFORMATION: 3,4 dihydroxy variant of Phe
<220> FEATURE:
<221> NAME/KEY: MOD_RES
<222> LOCATION: (6)..(6)
<223> OTHER INFORMATION: amidation of Asp

<400> SEQUENCE: 15

Phe Phe Phe Arg Gly Asp
1               5

<210> SEQ ID NO 16
<211> LENGTH: 6
<212> TYPE: PRT
<213> ORGANISM: Artificial Sequence
<220> FEATURE:
<223> OTHER INFORMATION: Peptide 3
<220> FEATURE:
<221> NAME/KEY: MOD_RES
<222> LOCATION: (1)..(1)
<223> OTHER INFORMATION: 3,4 dihydroxy variant of Phe
<220> FEATURE:
<221> NAME/KEY: MOD_RES
<222> LOCATION: (3)..(3)
<223> OTHER INFORMATION: 4F variant of Phe
<220> FEATURE:
<221> NAME/KEY: MOD_RES
<222> LOCATION: (5)..(5)
<223> OTHER INFORMATION: 4F variant of Phe
<220> FEATURE:
<221> NAME/KEY: MOD_RES
<222> LOCATION: (6)..(6)
<223> OTHER INFORMATION: amidation of Gly

<400> SEQUENCE: 16

Phe Asp Phe Arg Phe Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Peptide 4
<220> FEATURE:
<221> NAME/KEY: MOD_RES
<222> LOCATION: (1)..(1)
<223> OTHER INFORMATION: 3,4 dihydroxy variant of Phe (DOPA)
<220> FEATURE:
<221> NAME/KEY: MOD_RES
<222> LOCATION: (2)..(2)
<223> OTHER INFORMATION: 4F variant of Phe
<220> FEATURE:
<221> NAME/KEY: MOD_RES
<222> LOCATION: (5)..(5)
<223> OTHER INFORMATION: 4F variant of Phe
<220> FEATURE:
<221> NAME/KEY: MOD_RES
<222> LOCATION: (6)..(6)
<223> OTHER INFORMATION: acid variant of Arg

<400> SEQUENCE: 17

Phe Phe Asp Gly Phe Arg
1               5

<210> SEQ ID NO 18
<211> LENGTH: 6
<212> TYPE: PRT
<213> ORGANISM: Artificial Sequence
<220> FEATURE:
```

```
<223> OTHER INFORMATION: Peptide 4a
<220> FEATURE:
<221> NAME/KEY: MOD_RES
<222> LOCATION: (1)..(1)
<223> OTHER INFORMATION: 3,4 dihydroxy variant of Phe (DOPA)
<220> FEATURE:
<221> NAME/KEY: MOD_RES
<222> LOCATION: (2)..(2)
<223> OTHER INFORMATION: 4F variant of Phe
<220> FEATURE:
<221> NAME/KEY: MOD_RES
<222> LOCATION: (5)..(5)
<223> OTHER INFORMATION: 4F variant of Phe
<220> FEATURE:
<221> NAME/KEY: MOD_RES
<222> LOCATION: (6)..(6)
<223> OTHER INFORMATION: amidation of Arg

<400> SEQUENCE: 18

Phe Phe Asp Gly Phe Arg
1               5
```

COMPOUNDS WITH DUAL ACTIVITY

SEQUENCE LISTING

The Sequence Listing submitted in text format (.txt) filed on Feb. 24, 2021, named "SequenceListing-2021-02-24.txt", created on Feb. 24, 2021 (4.87 KB), is incorporated herein by reference.

TECHNOLOGICAL FIELD

The invention generally provides novel antifouling compounds having dual activity.

BACKGROUND OF THE INVENTION

The physical, chemical and biochemical properties of implant surfaces are some of the most important issues in the design of biomedical devices, as the first interaction between the implant and the body occurs at the interface.

Biofouling is a process in which organisms and their by-products encrust a surface. In the case of bacteria, this process leads to the formation of a well-defined bacterial network, termed biofilm. Biofilms provide the bacteria with superior survival properties under exposure to antibiotics. Biofilm formation on medical devices and implants leads to severe infection which may result in patient death.

In implantation (for example dental implant or priodental implant), between the implant and the body tissue, gaps and cavities are present, into which bacteria can penetrate. Peri-implantitis is the destructive inflammatory process affecting the soft and hard tissues surrounding such implants.

WO2014/118779 [1] discloses high quality antifouling materials comprising antifouling and surface-adsorbing moieties which provide a good solution to biofouling.

Tosatti et al. [2] discloses peptide functionalized poly(L-lysine)-g-poly(ethylene glycol) on titanium.

Subbiahdoss et al. [3] discloses bacterial biofilm formation versus mammalian cell growth on titanium-based mono- and bi-functional coatings.

Implant fate is known to depend not only on the ability of bacteria to penetrate gaps between the implant and body tissues but also by the ability of the implant to attract, enhance and induce migration of cell lines onto the implant materials. De Crescenzo et al. [4] reports on a system of coatings comprising adhesion peptides such as those derived from extracellular matrix proteins.

REFERENCES

[1] WO2014/118779
[2] Tosatti et al., *Biomaterials*, 24, 494-4958, 2003
[3] Subbiahdoss et al., *Eur. Cells and Mater.*, 19, 205-213, 2010
[4] De Crescenzo et al., *Biomacromolecules*, 16, 1682-1694, 2015

GENERAL DESCRIPTION

The inventors of the present invention have developed a family of novel and highly improved antifouling materials which spontaneously self-assemble into films and promote or encourage adherence of cells. The novel materials of the invention are capable of attracting cells from multicellular organisms and preventing antifouling by unicellular organisms. The materials of the invention can be used in biotechnological processes with any eukaryotic cells including mammalian cells or plant cells.

In a first aspect, there is provided a compound comprising at least one antifouling moiety (or group), at least one surface-adsorbing moiety (or group), and at least one amino acid sequence promoting adherence of cells, wherein the at least one antifouling moiety is a fluorine (—F) atom or a group comprising at least one fluorine atom; said at least one surface-adsorbing moiety is selected amongst dihydroxy-amino acids and dihydroxy-amino acid containing groups.

In another aspect, there is provided use of a compound of the invention for preventing antifouling by unicellular organisms and for attracting cells from multicellular organisms.

In some embodiments, the antifouling agent is selected to be capable of preventing or arresting adsorption of proteins and/or (poly)saccharides and/or (poly)lipids to a surface.

The antifouling moiety is a fluorine atom or a group which comprises one or more fluorine atoms and/or fluorinated moieties. The fluorine atom(s) may be bonded to any atom, e.g., a carbon atom and may be situated along the antifouling moiety or at its end. The number of fluorine atoms on the antifouling moiety may be at least one.

In some embodiments, the antifouling moiety comprises between 1 and 20 fluorine atoms. In some embodiments, the moiety comprises 1 or 2 or 3 or 4 or 5 or 6 or 7 or 8 or 9 or 10 or 11 or 12 or 13 or 14 or 15 or 16 or 17 or 18 or 19 or 20 fluorine atoms and/or between 1 and 20 fluorinated moieties/groups, wherein each of the fluorinated moieties/groups comprises between 1 and 3 fluorine atoms.

In some embodiments, the antifouling element is a fluorinated carbon group. In some embodiments, the fluorinated carbon group is fluorine-substituted carbon group having one or more C—F bonds. In some embodiments, the antifouling moiety comprises 1 or 2 or 3 or 4 or 5 carbon groups, each comprising one or more fluorine atoms. In some embodiments, the fluorinated carbon group comprises or consists —CF, —$CF_2$, and —$CF_3$ group(s).

In some embodiments, the fluorinated carbon group is a substituted or unsubstituted alkyl group (carbon group having single C—C bonds), substituted or unsubstituted alkenyl group (carbon group having at least one C=C bond) or substituted or unsubstituted alkynyl group (carbon group having at least one C≡C bond). In some embodiments, the substituted or unsubstituted carbon group, as defined is a $C_1$-$C_{20}$ group (being alkyl, alkenyl or alkynyl or mid group equivalents) comprising between 1 and 20 fluorine atoms. Where the group comprises a double bond or a single bond, the minimum number of carbon atoms in the group is 2, and thus the length of the carbon group, or the number of carbon atoms in the group may be selected and adjusted accordingly.

In some embodiments, the substituted or unsubstituted carbon group is selected from a $C_1$-$C_{19}$, $C_1$-$C_{18}$, $C_1$-$C_{17}$, $C_1$-$C_{16}$, $C_1$-$C_{15}$, $C_1$-$C_{14}$, $C_1$-$C_{13}$, $C_1$-$C_{12}$, $C_1$-$C_{11}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{20}$, $C_2$-$C_{19}$, $C_2$-$C_{18}$, $C_2$-$C_{17}$, $C_2$-$C_{16}$, $C_2$-$C_{15}$, $C_2$-$C_{14}$, $C_2$-$C_{13}$, $C_2$-$C_{12}$, $C_2$-$C_{11}$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{20}$, $C_3$-$C_{19}$, $C_3$-$C_{18}$, $C_3$-$C_{17}$, $C_3$-$C_{16}$, $C_3$-$C_{15}$, $C_3$-$C_{14}$, $C_3$-$C_{13}$, $C_3$-$C_{12}$, $C_3$-$C_{11}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{20}$, $C_4$-$C_{19}$, $C_4$-$C_{18}$, $C_4$-$C_{17}$, $C_4$-$C_{16}$, $C_4$-$C_{15}$, $C_4$-$C_{14}$, $C_4$-$C_{13}$, $C_4$-$C_{12}$, $C_4$-$C_{11}$, $C_4$-$C_{10}$, $C_4$-$C_9$, $C_4$-$C_8$, $C_4$-$C_7$, $C_4$-$C_6$, $C_4$-$C_5$, $C_5$-$C_{20}$, $C_5$-$C_{19}$, $C_5$-$C_{18}$, $C_5$-$C_{17}$, $C_5$-$C_{16}$, $C_5$-$C_{18}$, $C_5$-$C_{14}$, $C_5$-$C_{13}$, $C_5$-$C_{12}$, $C_5$-$C_1$, $C_5$-$C_{10}$, $C_5$-$C_9$, $C_5$-$C_8$, $C_5$-$C_7$, $C_5$-$C_6$, $C_6$-$C_{20}$, $C_6$-$C_{19}$, $C_6$-$C_{18}$, $C_6$-$C_{17}$, $C_6$-$C_{16}$, $C_6$-$C_{18}$, $C_6$-$C_{14}$, $C_6$-$C_{13}$, $C_6$-$C_{12}$, $C_6$-$C_{11}$, $C_6$-$C_{10}$, $C_6$-$C_9$, $C_6$-$C_8$, $C_6$-$C_7$, $C_7$-$C_{20}$, $C_7$-$C_{19}$, $C_7$-$C_{18}$, $C_7$-$C_{17}$, $C_7$-$C_{16}$, $C_7$-$C_{18}$, $C_7$-$C_{14}$, $C_7$-$C_{13}$, $C_7$-$C_{12}$, $C_7$-$C_{11}$, $C_7$-$C_{10}$, $C_7$-$C_9$, $C_7$-$C_5$, $C_5$-$C_{20}$, $C_5$-$C_{19}$, $C_5$-$C_{18}$, $C_5$-$C_{17}$, $C_5$-$C_{16}$, $C_5$-$C_{15}$, $C_5$-$C_{14}$, $C_5$-$C_{13}$, $C_5$-$C_{12}$, $C_5$-$C_{11}$, $C_5$-$C_{10}$, $C_5$-$C_9$, $C_9$-$C_{20}$, $C_9$-$C_{19}$, $C_9$-$C_{15}$, $C_9$-$C_{17}$, $C_9$-$C_{16}$, $C_9$-$C_{18}$, $C_9$-$C_{14}$, $C_9$-$C_{13}$, $C_9$-$C_{12}$, $C_9$-$C_{11}$, $C_9$-$C_{10}$, $C_{10}$-$C_{20}$, $C_{10}$-$C_{19}$, $C_{10}$-$C_{18}$, $C_{10}$-$C_{17}$, $C_{10}$-$C_{16}$, $C_{10}$-$C_{18}$, $C_{10}$-$C_{14}$, $C_{10}$-$C_{13}$, $C_{10}$-$C_{12}$, $C_{10}$-$C_{11}$, $C_1$-$C_{20}$, $C_1$-$C_{19}$, $C_{11}$-$C_{19}$, $C_{11}$-$C_{18}$, $C_{11}$-$C_{17}$, $C_1$-$C_{16}$, $C_{11}$-$C_{15}$, $C_1$-$C_{14}$, $C_1$-$C_{13}$, $C_1$-$C_{12}$, $C_{12}$-$C_{20}$, $C_{12}$-$C_{19}$, $C_{12}$-$C_{15}$, $C_{12}$-$C_{17}$, $C_{12}$-$C_{16}$, $C_{12}$-$C_{18}$, $C_{12}$-$C_{14}$, $C_{12}$-$C_{13}$, $C_{13}$-$C_{20}$, $C_{13}$-$C_{19}$, $C_{13}$-$C_{17}$, $C_{13}$-$C_{16}$, $C_{13}$-$C_{18}$, $C_{12}$-$C_{14}$, $C_{14}$-$C_{20}$, $C_{14}$-$C_{19}$, $C_{14}$-$C_{15}$, $C_{14}$-$C_{17}$, $C_{14}$-$C_{16}$, $C_{14}$-$C_{15}$, $C_{15}$-$C_{20}$, $C_{15}$-$C_{19}$, $C_{15}$-$C_{18}$, $C_{15}$-$C_{17}$, $C_{15}$-$C_{16}$, $C_{16}$-$C_{20}$, $C_{16}$-$C_{19}$, $C_{16}$-$C_{18}$, $C_{16}$-$C_{17}$, $C_{17}$-$C_{20}$, $C_{17}$-$C_{19}$, $C_{17}$-$C_{18}$, $C_{15}$-$C_{20}$, $C_{15}$-$C_{19}$ and $C_{19}$-$C_{20}$.

In some embodiments, the fluorinated carbon group is a $C_1$-$C_{20}$ group comprising between 1 and 20 fluorine atoms or a $C_2$-$C_{20}$ group comprising between 1 and 20 fluorine atoms.

In some embodiments, the substituted or unsubstituted carbon group comprises 1, 2, 3, 4, 5, 6, 7, 8, 9, 10, 11, 12, 13, 14, 15, 16, 17, 18, 19 or 20 carbon atoms.

In some embodiments, the fluorinated carbon group is perfluorinated (containing only carbon-fluorine bonds (no C—H bonds) and C—C bonds; other heteroatoms may be present). In some embodiments, only the alkyl, alkenyl or alkynyl moieties or groups are perfluorinated, while other moieties or groups present in a compound of the invention are not fluorinated or not perfluorinated.

As disclosed below, the fluorinated group may be an end-group or a mid-group, in which case the alkyl group is an alkylene group, similarly defined as the alkyl group to comprise carbon atoms according to embodiments of the invention, the alkenyl group is an alkenylene, similarly defined, and the alkynyl group is an alkynylene, similarly defined as the alkyl group to comprise carbon atoms according to embodiments of the invention.

In some embodiments, the antifouling moiety is an alkyl. In some embodiments, the alkyl group comprising 1 or 2 or 3 or 4 or 5 or 6 or 7 or 8 or 9 or 10 fluorine atoms. In some embodiments, the antifouling moiety is an alkyl having at least one fluorine atom on each carbon atom.

In other embodiments, the antifouling moiety is a fluorinated substituted or unsubstituted aryl, which may comprise one or more aromatic or heteroaromatic ring systems. The aryl group may be a phenyl group, a substituted phenyl group, a bi- or multi-phenyl system, a fused ring-system (e.g., naphthyl), a multicyclic ring-system or a heteroaryl (which may be a fused or a multicyclic ring-system), each of which being optionally substituted.

In some embodiments, the aryl comprises 1 or 2 or 3 or 4 or 5 fluorine atoms. In some embodiments, where the aryl comprises a single aromatic ring, the ring may be fluorinated by 1 or 2 or 3 or 4 or 5 fluorine atoms. Where the aryl is multicyclic or a fused ring system, such as a naphthyl, each ring in the multicyclic or fused system may comprise at least one fluorine atoms. In some embodiments, the aryl is perfluorinated.

In other embodiments, the aryl is a phenyl group. In other embodiments, the aryl is a fused system, e.g., nathpthyl. In some embodiments, the aryl is a heteroaryl group.

In some embodiments, the phenyl group is substituted or unsubstituted.

In some embodiments, the antifouling moiety comprises or consists one or more fluorinated amino acid moieties.

In some embodiments, the fluorinated amino acid is a fluorinated phenylalanine derivative, wherein the fluorine atom substitutes one or more phenyl ring positions. The substitution on the phenyl ring may be at the ortho, meta and/or para positions. The number of fluoride atoms may be 1, 2, 3, 4, or 5.

In some embodiments, the fluorinated phenylalanine is selected from o-fluorophenylalanine, m-fluorophenylalanine and p-fluorophenylalanine.

In some embodiments, a compound of the invention is an antifouling agent capable of preventing or arresting adsorption of organic and/or bio-organic materials (polymers) to a surface (an article's surface) and at the same time capable of promoting and encouraging attachment of cells to the surface. The ability to promote and encourage such attachment of cells is through an amino acid sequence present in a compound of the invention. The at least one "amino acid sequence promoting adherence of cells" is an amino acid sequence of three or more amino acids, as defined herein, forming as a minimum a tripeptide, and which is selected (inter alia in terms of amino acid identity, connectivity, number of amino acids and sequence length) to provide increased adherence to or adhesiveness of cells. In some embodiments, the amino acid sequence is a truncated fragment of fibronectin which binds integrins (see "Protein-protein Recognition" By Colin Kleanthous). In some embodiments, the truncated fragment is RGD or a fragment comprising RGD.

In some embodiments, the at least one amino acid sequence promoting adherence of cells include amino acid sequences comprising or consisting a sequence selected from RGD; VRN; and SEQ ID NOs. 1-13 (wherein each letter designates an amino acid as known in the art).

In some embodiments, the at least one amino acid sequence is RGD (Arg-Gly-Asp).

In some embodiments, the at least one amino acid sequence is SEQ ID NO. 1 RGDS (Arg-Gly-Asp-Ser).

Thus, in another aspect there is provided a compound comprising at least one surface binding moiety (or group), at least one moiety comprising at least one fluorine atom and an amino acid sequence Arg-Gly-Asp or Arg-Gly-Asp-Ser (SEQ ID NO. 1), wherein each of said moieties being covalently bonded to at least one of the other moieties.

In another aspect, there is provided an antifouling material comprising the amino acid sequence Arg-Gly-Asp or Arg-Gly-Asp-Ser (SEQ ID NO. 1).

In some embodiments, the antifouling material comprises at least one fluorinated moiety, as defined.

In accordance with the invention, the compounds are selected to self-assemble into films. Thus, when provided on a surface region of a substrate, the material associate with the surface region via at least one surface-adsorbing moiety. The surface binding moiety is one having at least one atom or group of atoms capable of interacting, e.g., by adsorption, to at least one surface region. In some embodiments, the at least one surface binding moiety is selected amongst 3,4-dihydroxy-L-phenylalanin (DOPA), a DOPA containing moiety and dopamine.

The at least one surface binding moiety, e.g., DOPA or a DOPA containing moiety, is configured to adhere, adsorb or associate with a surface or a region of a surface which protection against fouling is desired. The term "associate" or "adhere" or "adsorb", as used herein, refers to any physical or chemical interaction to be formed between the surface and the DOPA group or any atom thereof. The association may be via Van-der-Walls, coordinative, covalent, ionic, electrostatic, dipole-dipole, or hydrogen association (bond or interaction).

Independently of the actual nature of the surface-adsorbing group, namely whether it is DOPA or a DOPA derivative, and whether association occurs via a single atom or a group of atoms or via multiple atoms, the surface-adsorbing moiety (element) is capable of adhering and/or capable of maintaining the surface adherence to any surface material. The surface adherence may be maintained even under non-dry conditions such as under aquatic environment, and also under harsher conditions such as high salt concentrations.

In some embodiments, the compounds of the invention comprise one or more DOPA or DOPA-containing groups. Where a compound comprises more than one DOPA group or a DOPA-containing group, the groups may or may not be bonded to each other. In some cases, the more than one DOPA or DOPA-containing groups may be separated by one or more groups, as defined.

As known, DOPA comprises two hydroxyl (—OH) groups. Without wishing to be bound by theory, it is believed that surface adsorption occurs via one or both of said hydroxyl groups. In some embodiments, the DOPA group or a moiety comprising DOPA may be modified to comprise one or more additional hydroxyl groups. In some embodiments, each compound of the invention comprises two or more DOPA groups or moieties comprising DOPA groups. In some embodiments, each compound of the invention comprises three or more DOPA groups or moieties comprising DOPA groups.

In some embodiments, a compound of the invention comprises 2, 3, 4, 5, 6, 7, 8, 9, or 10 DOPA groups or moieties comprising DOPA groups. In some embodiments, a compound of the invention comprises 2, 3, 4 or 5 DOPA groups or moieties comprising DOPA groups. In some embodiments, a compound of the invention comprises 2 or 3 or 4 DOPA groups or moieties comprising DOPA groups. In some embodiments, a compound of the invention comprises 2 or 3 DOPA groups or moieties comprising DOPA groups.

In some embodiments, the moiety comprising DOPA is an organic material selected from amino acids and aliphatic materials (aliphatics as known in the art). In some embodiments, the organic material is an amino acid. In other embodiments, the material is a peptide.

In some embodiments, the DOPA is linked, associated or bonded to an atom along a linker moiety. In some embodiments, the linker is selected from substituted or unsubstituted carbon chains or groups. In some further embodiments, the linker is composed of two or more amino acids. In some embodiments, the linker comprises between 1 to 40 carbon atoms.

In some embodiments, the linker is of the general structure

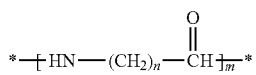

wherein
each * denotes a point of connectivity;
n is between 0 and 40; and
m is between 1 and 40.

In some embodiments, the compound comprises a DOPA unit as well as at least one additional hydroxylated moiety. The hydroxylated moiety may be selected amongst mono-, di-, tri-, tetra- or multiply-hydroxylated alkyls and aryl groups and hydroxylated amino acids.

In some embodiments, the DOPA is associated with at least one amino acid.

As used herein, with reference to any "amino acid", the term relates to natural, non-natural in a D- or L-configuration or a peptidomemetics. The amino acid may be an alpha amino acid or a beta amino acid, as known in the art.

In some embodiments, the term indicates an amino acid selected from naturally occurring amino acids and synthetic or semi-synthetic amino acids. In some embodiments, the amino acid is selected amongst alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine valine, pyrrolysine and selnocysteine; and amino acid analogs such as homo-amino acids, N-alkyl amino acids, dehydroamino acids, aromatic amino acids and α,α-disubstituted amino acids, cystine, 5-hydroxylysine, 4-hydroxyproline, α-aminoadipic acid, α-amino-n-butyric acid, 3,4-dihydroxyphenyl alanine, homoserine, α-methylserine, omithine, pipecolic acid, ortho, meta or para-aminobenzoic acid, citrulline, canavanine, norleucine, d-glutamic acid, aminobutyric acid, L-fluorenylalanine, L-3-benzothienylalanine and thyroxine.

In some embodiments, the at least amino acid is an amino acid comprising at least one aromatic ring. In some embodiments, said amino acid comprising at least one aromatic ring is selected from tryptophan, tyrosine, naphthylalanine and phenylalanine.

In some embodiments, the amino acid is phenylalanine or a derivative thereof. In some embodiments the phenylalanine derivative is selected from 4-methoxy-phenylalanine, 4-carbamimidoyl-1-phenylalanine, 4-chloro-phenylalanine, 3-cyano-phenylalanine, 4-bromo-phenylalanine, 4-cyano-phenylalanine, 4-hydroxymethyl-phenylalanine, 4-methyl-phenylalanine, 1-naphthyl-alanine, 3-(9-anthryl)-alanine, 3-methyl-phenylalanine, m-amidinophenyl-3-alanine, phenylserine, benzylcysteine, 4,4-biphenylalanine, 2-cyano-phenylalanine, 2,4-dichloro-phenylalanine, 3,4-dichloro-phenylalanine, 2-chloro-penylalanine, 3,4-dihydroxy-phenylalanine, 3,5-dibromotyrosine, 3,3-diphenylalanine, 3-ethyl-phenylalanine, 3,4-difluoro-phenylalanine, 3-chloro-phenylalanine, 3-chloro-phenylalanine, 2-fluoro-phenylalanine, 3-fluoro-phenylalanine, 4-amino-L-phenylalanine, homophenylalanine, 3-(8-hydroxyquinolin-3-yl)-1-alanine, 3-iodo-tyrosine, kynurenine, 3,4-dimethyl-phenylalanine, 2-methyl-phenylalanine, m-tyrosine, 2-naphthyl-alanine, 5-hydroxy-1-naphthalene, 6-hydroxy-2-naphthalene, meta-nitro-tyrosine, (beta)-beta-hydroxy-1-tyrosine, (beta)-3-chloro-beta-hydroxy-1-tyrosine, o-tyrosine, 4-benzoyl-phenylalanine, 3-(2-pyridyl)-alanine, 3-(3-pyridyl)-alanine, 3-(4-pyridyl)-alanine, 3-(2-quinolyl)-alanine, 3-(3-quinolyl)-alanine, 3-(4-quinolyl)-alanine, 3-(5-quinolyl)-alanine, 3-(6-quinolyl)-alanine, 3-(2-quinoxalyl)-alanine, styrylalanine, pentafluoro-phenylalanine, 4-fluoro-phenylalanine, phenylalanine, 4-iodo-phenylalanine, 4-nitro-phenylalanine, phosphotyrosine, 4-tert-butyl-phenylalanine, 2-(trifluoromethyl)-phenylalanine, 3-(trifluoromethyl)-phenylalanine, 4-(trifluoromethyl)-phenylalanine, 3-amino-L-tyrosine, 3,5-diiodotyrosine, 3-amino-6-hydroxy-tyrosine, tyrosine, 3,5-difluoro-phenylalanine and 3-fluorotyrosine.

In some embodiments, the amino acid is fluorinated. Fluorinated amino acids may be an amino acid selected from o-fluorophenylalanine, m-fluorophenylalanine and p-fluoro-phenylalanine.

In some embodiments, the fluorinated antifouling group is a fluorinated amino acid, as defined.

In some embodiments, the compound comprises between 2 and 12 amino acids, at least one of the amino acids being selected from aromatic amino acids.

As stated herein, compounds of the invention comprise the three functional moieties: at least one antifouling moiety, the at least one surface-adsorbing moiety and the at least one amino acid sequence promoting adherence of cells. Each of the three functional moieties are associated to each other via a non-hydrolysable bond or via a linker group, as defined. In some embodiments, the non-hydrolysable bond is a covalent bond. In some embodiments, the bond is a peptide bond.

Six possible combinations of the three moieties are provided in accordance with the invention, and as further detailed herein. For the sake of simplicity, the three moieties are designated as follows: J is the at least one surface binding moiety, X is the at least one antifouling moiety and Z is the amino acid sequence promoting adherence of cells. Compounds of the invention may thus be in a form selected from: J-X—Z, J-Z—X, X—Z-J, X-J-Z, Z—X-J or Z-J-X; wherein each "-" designates a covalent bond or a linker moiety.

In some embodiments, the linker moiety is selected from substituted or unsubstituted carbon chains. In some further embodiments, the linker is composed of two or more amino acids. In some embodiments, the linker comprises between 1 to 40 carbon atoms. In some embodiments, the linker moiety is of the general structure:

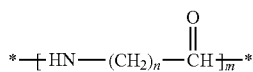

wherein
each * denotes a point of connectivity;
n is an integer between 0 and 40; and
m is an integer between 1 and 40.

In some embodiments of the invention, the compound of the invention is of the general structure of Formula (I):

wherein
J is a surface binding moiety,
X is an antifouling moiety,
Z is the amino acid sequence promoting adherence of cells, e.g., RGD, and each "-" designates a covalent bond or a linker moiety.

In some embodiments, the surface binding moiety, J, is DOPA or a DOPA-containing group. In some embodiments, the compound is a compound of Formula (II):

wherein
X is an antifouling moiety,
Z is an amino acid sequence, e.g., RGD, and each "-" designates a covalent bond.

In some embodiments, X is a fluorinated group. In some embodiments, X is a fluorinated carbon group, as defined herein. In some embodiments, the carbon group is perfluorinated. In some embodiments, X is a fluorinated amino acid, wherein the amino acid is as defined herein.

In some embodiments, in a compound of the general Formula (I), each "-" designates a peptide bond. In such embodiments, in a compound of Formula (I) or (II), each of J and X may be a single or two or more amino acids, which may or may not be the same.

In some embodiments, a compound of the general Formula (I) has an end of chain J moiety and an end of chain Z moiety, wherein the antifouling moiety X may comprise one or more amino acids, one of which being a fluorinated amino acid, optionally X being connected or bonded to either J and/or Z via a linker moiety, as defined.

In some embodiments, in a compound of the general Formula (I), J is DOPA, X is a fluorinated phenylanlanine and Z is the tripeptide RGD, wherein each "-" signifies a peptide bond.

In some embodiments, in a compound of Formula (I), the moiety J-X may comprise between 2 (in case each J and X is a single amino acid, as defined) and 40, or between 2 and amino acids, or between 2 and 12 amino acids or between 2 and 8 amino acids; each amino acid being bonded to at least one neighboring amino acid via a peptide (amide) bond.

In some embodiments, in a compound of Formula (I), each of said J, X and Z may be present once or several times. Thus, a compound of the general Formula (I) may be in the form of general Formula (III):

wherein each of J, X and Z are as defined herein and each of n, m and k, independently of the other, is an integer defining the number of respective moieties in the compound; the integers being between 1 and 10.

In a compound of the general Formula (III), each of J, X and Z, independently, may appear once or more times; where at least one of J, X and Z, independently, is present multiple times, it need not appear in sequence. Thus, multiple J, X and/or Z, independently, need not be grouped. Examples of such compounds of the invention include compounds of the general formulae J-J-X—Z-J, J-X—Z—X—X, X—Z-J-J-Z—X, J-X—X—Z, J-J-X—X—Z, J-J-J-X—X-X-Z, X—X-X-J-J-X—X-X-Z and others, wherein each of J, X and Z is as defined, and wherein the repeating moieties may or may not be the same. For example, in a compound having the general structure J-X—X—Z, each of the two X moieties may or may not be the same.

In some embodiments, a compound according to the invention is the compound having the structure of Formula (IV):

wherein each of J, X and Z are as defined herein, and wherein each of the two X groups may or may not be the same.

In some embodiments, the compound of the formula (IV) is exemplified by the compound DOPA-Phe(4F)-Phe(4F)-Arg-Gly-Asp, herein designated Peptide 1, which full structure is shown below. From the presented structure below, one can understand how the various moieties discussed and exemplified herein may be connected in order to establish a compound which has the dual function of antifouling and cell adhesion, in addition to its ability to surface-associate.

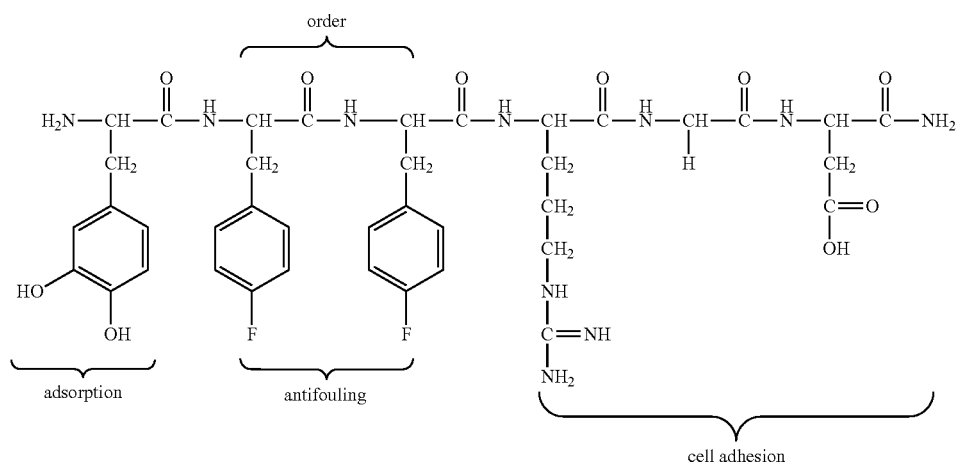

In some embodiments, the compound of general Formula (I) is a tripeptide. In some embodiments, the compound of general Formula (I) is a tetrapeptide. In some embodiments, the compound of general Formula (I) is a pentapeptide. In some embodiments, the compound of general Formula (I) is a hexapeptide.

In some embodiments, in a compound of Formula (I) each of X and J is different from an amino acid(s) (namely, each of X and J are not amino acids, as defined) and Z is as defined.

In some embodiments, in a compound of Formula (I), only one of X, J and Z is or comprises an amino acid. In some embodiments, in a compound of Formula (I), only two of X, J and Z are or comprise amino acid(s). In some embodiments, in a compound of Formula (I), each of X, J and Z is or comprises an amino acid(s).

In some embodiments, the compound of Formula (I) is at least a pentapeptide, namely comprising at least 5 amino acids, at least one being X, at least one being J and at least one of which being Z.

In some embodiments, the compound of Formula (I) is at least a pentapeptide, namely comprising at least 5 amino acids, at least two of which being X, at least two of which being J and at least one of which being Z. In some embodiments, the compound of Formula (I) is at least a pentapeptide, namely comprising at least 5 amino acids, at least two of which being X, at least one of which being J and at least two of which being Z. In some embodiments, the compound of Formula (I) is at least a pentapeptide, namely comprising at least 5 amino acids, at least three of which being X, at least one of which being J and at least one of which being Z. In some embodiments, the compound of Formula (I) is at least a pentapeptide, namely comprising at least 5 amino acids, at least one of which being X, at least three of which being J and at least one of which being Z.

In some embodiments, the compound of Formula (I) is at least a hexapeptide, namely comprising at least 6 amino acids, at least one being X, at least one being J and at least one of which being Z.

In some embodiments, the compound of Formula (I) is at least a hexapeptide, namely comprising at least 6 amino acids, at least two of which being X, at least two of which being J and at least two of which being Z. In some embodiments, the compound of Formula (I) is at least a hexapeptide, namely comprising at least 6 amino acids, at least two of which being X, at least two of which being J and at least one of which being Z. In some embodiments, the compound of Formula (I) is at least a hexapeptide, namely comprising at least 6 amino acids, at least three of which being X, at least two of which being J and at least one of which being Z. In some embodiments, the compound of Formula (I) is at least a hexapeptide, namely comprising at least 6 amino acids, at least two of which being X, at least three of which being J and at least one of which being Z.

In some embodiments, the compound of Formula (I) is a pentapeptide or a hexapeptide of the general Formula (V) or Formula (VI):

X—X-J-Z     (V)

Z—X—X-J     (VI)

wherein each of X, J and Z is as defined herein, and wherein each of the X groups may or may not be the same.

In some embodiments, the group Z is selected from RGD and RGDS (SEQ ID NO. 1).

In some embodiments, the compound is a hexapeptide. In some embodiments, the hexapeptide is selected from:

J-X—X-RGD     (VII, an example is Peptide 1)

X—X-J-RGD     (VIII, an example is Peptide 2)

RGD-X—X-J     (IX)

(SEQ ID NO. 1) RGDS-X—X-J     (X) and

X—X-J-RGDS (SEQ ID NO. 1)     (XI).

In some embodiments, the compound is a peptide herein designated Peptide 2, having the full structure:

The invention further provides a compound selected from Peptide 1 and Peptide 2.

Where surface antifouling activity and promotion of cell adherence are desired, a compound J-X—Z of the general Formula (I), as defined, may be replaced with a formulation comprising a combination of two or more peptides selected from J-X, X—Z, J-Z and X-J, wherein each of J, X, Z and "-" are as defined herein; provided that the combination comprises at least one peptide having moiety J, at least one peptide having moiety X and at least one peptide having moiety Z.

In some embodiments, the combination comprises J-X or X-J and at least one of X—Z and J-Z. In some embodiments, the combination comprises X—Z and at least one of J-X, X-J and J-Z. In some embodiments, the combination comprises J-Z and at least one of J-X, X-J and X—Z. As a person versed in the art would realize, the peptides J-X and X-J are different in the way the two peptides are bonded. In one case, amino acid J is connected to amino acid X via its amine group, while in the other case, J is bonded to X via its carboxylic acid group.

In another aspect, the invention provides a formulation comprising a compound of the invention or a combination of the invention, each as defined herein.

In some embodiments, the formulation comprises at least one compound according to any of the Formulae of the invention, e.g., J-X—Z ($J_n$-$X_m$—$Z_k$), as defined, in combination with at least one of peptides selected from J-X, X—Z, J-Z and X-J, as defined.

In some embodiments, the formulation is adapted for forming a film of a compound or combination of compounds/peptides, as defined, on a surface region. In some embodiments, the formulation comprises at least one volatile liquid carrier which carries the compound or combination in solution, as a suspension or as dispersion.

In some embodiments, the formulation is configured to provide a film capable of promoting attachment of cells thereonto and/or capable of reducing biofouling.

In some embodiments, the formulation is utilized in a method of implantation (e.g., establishing an implant in vivo, in situ). In some embodiments, the formulation is configured to provide a film on a surface region of an implantable device or object.

In other embodiments, the formulation is utilized in a biotechnological process involving adherence of cells, e.g., eukaryotic cells, to a surface, while preventing biofouling. In some embodiments, the surface may be a surface region of a biotechnological device such as a reactor used in biotechnology.

In further embodiments, the formulation of the invention, as the compounds themselves, may be utilized in processes or appropriate technologies wherein enhancement or otherwise modulation of cell adherence is required at a fouling-free environment.

In some embodiments, the film is adapted for preventing contamination by an organism at the implantation site. In some embodiments, the film is configured for preventing biofouling caused by an organism.

In some embodiments, the microorganism is selected from bacteria, diatoms, hydroids, algae, bryozoans, protozoans and ascidians.

In some embodiments, the organism is bacteria. In some embodiments, the bacteria is selected from *Bordetella pertussis, Borrelia burgdorferi, Brucella abortus, Brucella canis, Brucella melitensis, Brucella suis, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli (E. coli)*, Enterotoxigenic *Escherichia coli* (ETEC), Enteropathogenic *E. coli, Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitidis, Pseudomonas aeruginosa, Rickettsia rickettsii, Salmonella typhi, Salmonella typhimurium, Shigella sonnei, Staphylococcus epidermidis, Staphylococcus saprophyticus, Streptococcus agalactiae, Streptococcus mutans Streptococcus pneumonia, Streptococcus pyogenes, Treponema pallidum, Vibrio cholera, Vibrio harveyi* and *Yersinia pestis*.

In some embodiments, the bacterium is *Escherichia coli* (*E. Coli*). In some other embodiments, the bacterium is *P. aeruginosa*.

In some embodiments, the film is adapted for inducing attachment of cells onto a surface region of the implantable device or object.

As used herein, the term "implant" refers to any medical device, e.g., medical devices that are adapted for insertion into a body cavity. An implant of the invention is manufactured to be inserted in the body in order to facilitate proper bodily function or treat at least one clinical condition. Some implants replace a missing biological structure, support a damaged biological structure, or enhance an existing biological structure. In some other embodiments, an implant can provide a function clinically needed by the subject. The surface of the implant coming into contact with a body region or organ or tissue may be of a biomedical material such as titanium, silicone or apatite. The implant may be dental, orthodental, orthopedic etc.

In some embodiments, the implant is a bone implant and the film formed thereon is suitable for anchoring osteoclasts or osteoblasts on the implant surface.

Thus, in another aspect, the invention provides a method of anchoring or attracting cells onto a surface region of an implantable device or object, said method comprising forming on a surface region of the implantable device or object a film of a compound or combination according to the invention and implanting said device or object, wherein the film promotes anchoring or attachment of cells thereto.

As used herein, the term "cells" refers to cells such as to osteoblasts or osteoclasts.

In another aspect, the invention provides a method of reducing biofouling caused by an organism on an implant post-operative placement of said implant in a body cavity or in contact with a tissue, said method comprising forming on a surface region of the implant a film of a compound or combination according to the invention and implanting said implant, wherein the film promotes anchoring or attachment of cells thereto.

In another aspect, the invention provides a method of attracting body cells to and reducing biofouling on an implant, said method comprising forming a film of a compound or combination according to the invention on a surface region of the implant and implanting said implant.

In another aspect, the invention provides a method for preventing, ameliorating, or treating a disease or disorder related to an implant having been placed in a body cavity or on a tissue, said method comprising the step of forming a film of a compound or a combination according to the invention on a surface region of an implant prior to implantation.

In some embodiments, the disease is peri-implantitis.

In another aspect, the invention provides a method for prolonging lifetime of an implant intended for implantation in a subject, said method comprising coating a surface region of the implant prior to implantation with a film comprising a compound or a combination according to the invention.

In another aspect, the invention provides a method for stimulating or encouraging bone healing or absorption of an implant after implantation, the method comprising coating a surface region of the implant prior to implantation with a compound or combination of the invention, thereby inducing bone healing.

In another aspect, the invention provides a medical device comprising a film of a compound or a combination according to the invention. In some embodiments, the implant is a dental implant. In some embodiments, the implant is a permanent implant.

In another aspect, the invention provides a kit comprising a formulation of a compound or a combination according to the invention and instructions of use.

As used herein, the subject may be a human or a non-human subject.

In some embodiments, the surface region of an implant is any one region of an implant surface, being optionally the full surface of the implant, as determined by a medical professional or one versed in the pertinent field.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2A: Ti Surface; FIG. 2B: surface coated with Peptide 1; FIG. 2C: surface coated with Peptide 2; FIG. 2D: surface coated with Peptide 3; and FIG. 2E: surface coated with Peptide 4.

FIG. 4A: Ti Surface; FIG. 4B: surface coated with Peptide 1; FIG. 4C: surface coated with Peptide 2; FIG. 4D: surface coated with Peptide 3; and FIG. 4E: surface coated with Peptide 4.

FIG. 5A: Ti Surface; FIG. 5B: surface coated with Peptide 1; FIG. 5C: surface coated with Peptide 2; FIG. 5D: surface coated with Peptide 3; and FIG. 5E: surface coated with Peptide 4.

DETAILED DESCRIPTION OF THE INVENTION

Numerous pentapeptides and hexapeptides according to the invention have been prepared and studied. For the sake of demonstrating the efficacy and uniqueness of the invention disclosed herein, the following hexapeptides have been prepared:

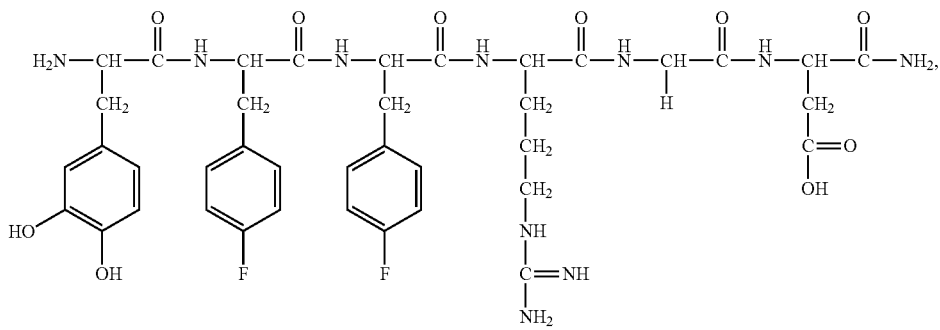

NH₂-DOPA-(4F)Phe-(4F)Phe-Arg-Gly-Asp-CONH₂ (Peptide 1)

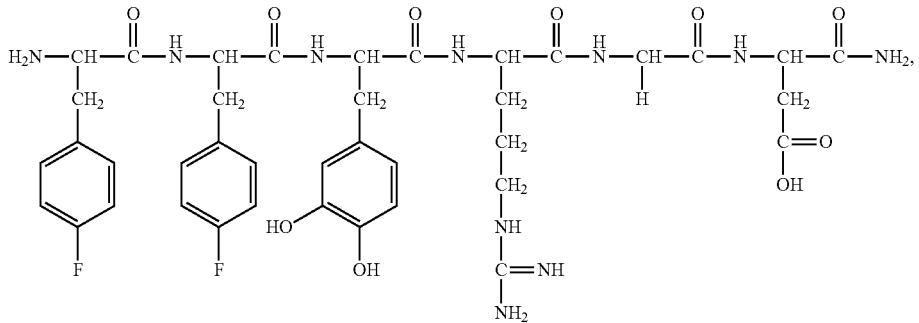

NH₂-(4F)Phe-(4F)Phe-DOPA-Arg-Gly-Asp-CONH₂ (Peptide 2)

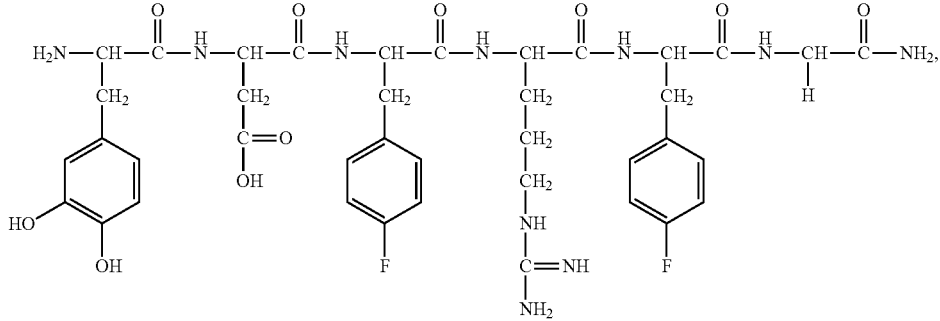

NH₂-DOPA-Asp-(4F)Phe-Arg-(4F)Phe-Gly-CONH₂ (Peptide 3)

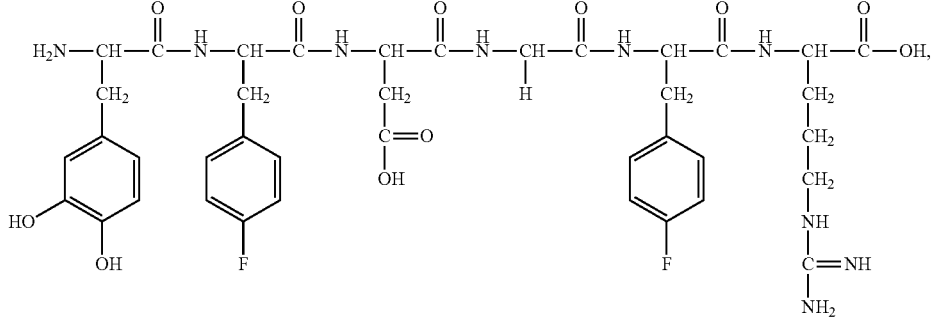

NH₂-DOPA-(4F)Phe-Asp-Gly-(4F)Phe-Arg-CONH₂ (Peptide 4)

and
NH₂-DOPA-(4F)Phe-Asp-Gly-(4F)Phe-Arg-CONH₂ (Peptide 4a) (SEQ ID NO. 18).

Figure 1:
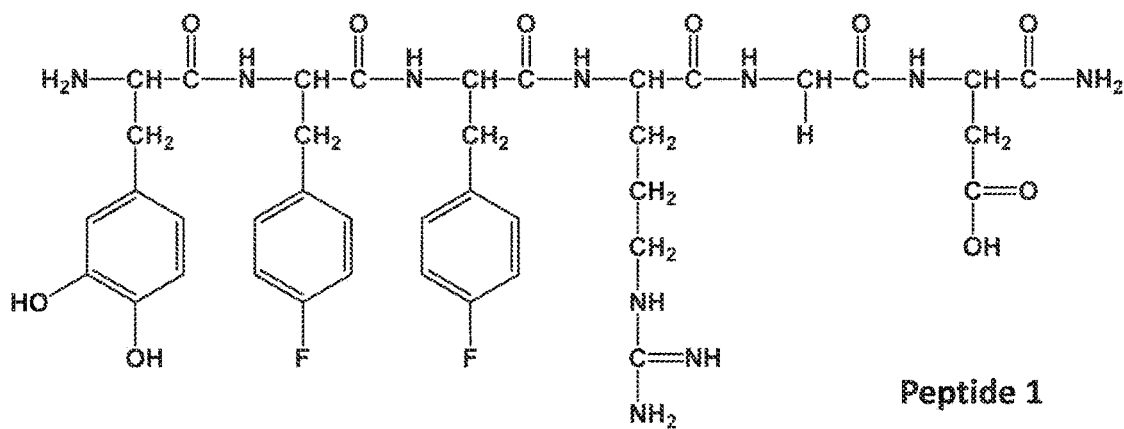
FIG. 1 provides structures of 4 peptides according to the invention. These peptides are non-limiting examples of peptides and compounds according to the invention.
Figure 1:
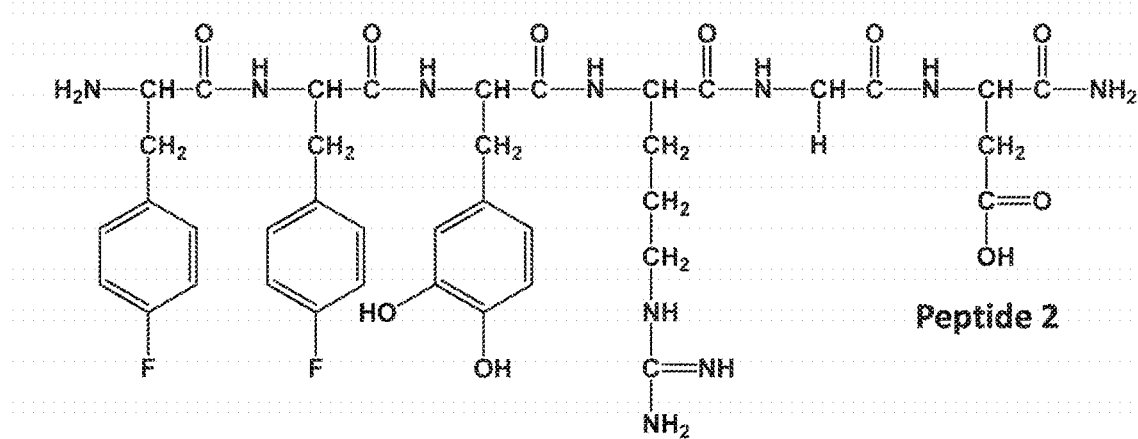
Figure 1:
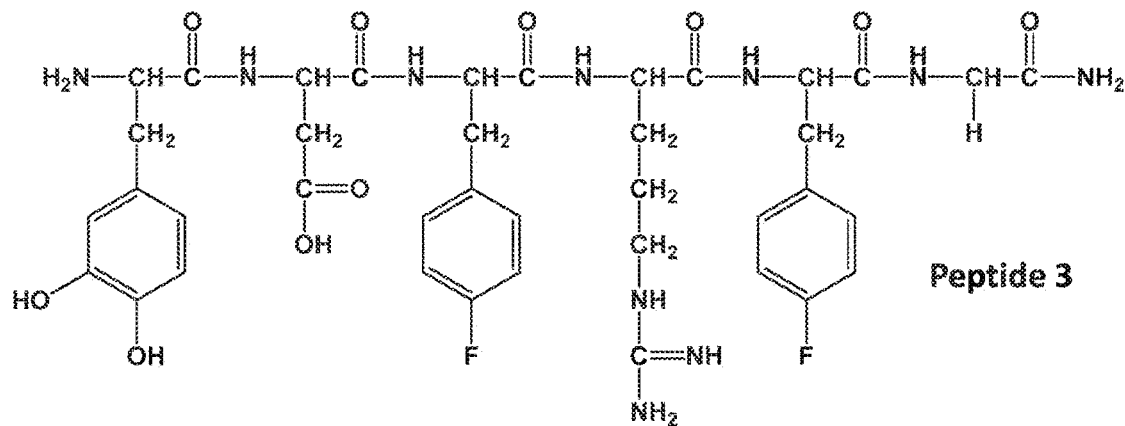
Figure 1:
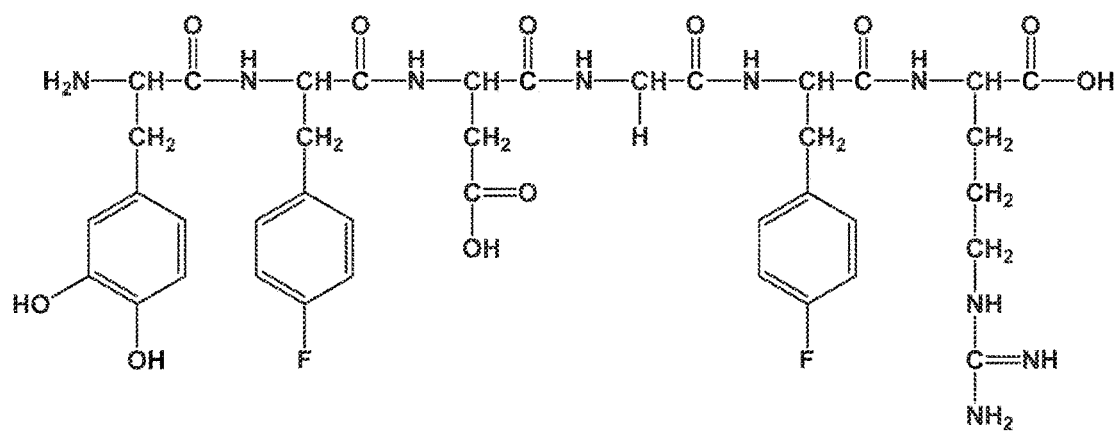
Figure 2A:
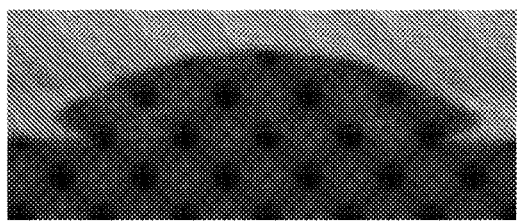
FIGS. 2A-E show changes in contact angle of surfaces coated with compounds of the invention.
Figure 2B:
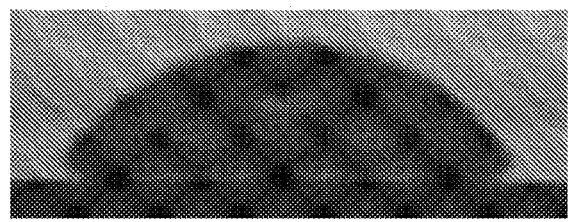
Figure 2C:
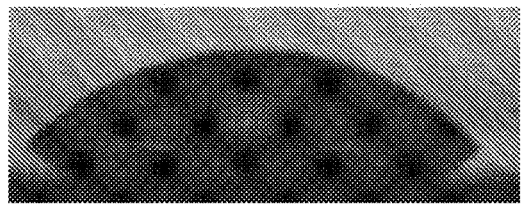
Figure 2D:
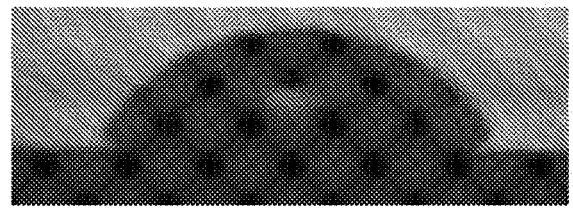
Figure 2E:

As shown in FIG. 1, Peptide 1 and Peptide 2 contain the di-(4F)Phe sequence and the RGD sequence together with DOPA amino acid but in different place in the sequence. In Peptide 3 and Peptide 4 the sequence of the amino acids was mixed to have control peptides which contain the same amino acids, but without the cell adhesion and the anti-fouling elements. The synthesis of the hexapeptides was performed by manually Fmoc-SPPS (solid-phase peptide synthesis). The peptides were purified to >95% purity.

To coat the Ti substrate with a peptide, a bare titanium substrate was dipped in 1 mg\ml peptide solution (Tris buffer). The change of the surface contact angle due to the assembly of the peptide on the substrate was measured.

As can be seen in FIGS. 2A-E, the coated surface exhibited an increase in the contact angle from 33°, in the case of titanium in buffer, to 54°, 49°, 55° and 65°, in the case of coating with Peptides 1, 2, 3 and 4, respectively.

Figure 3:
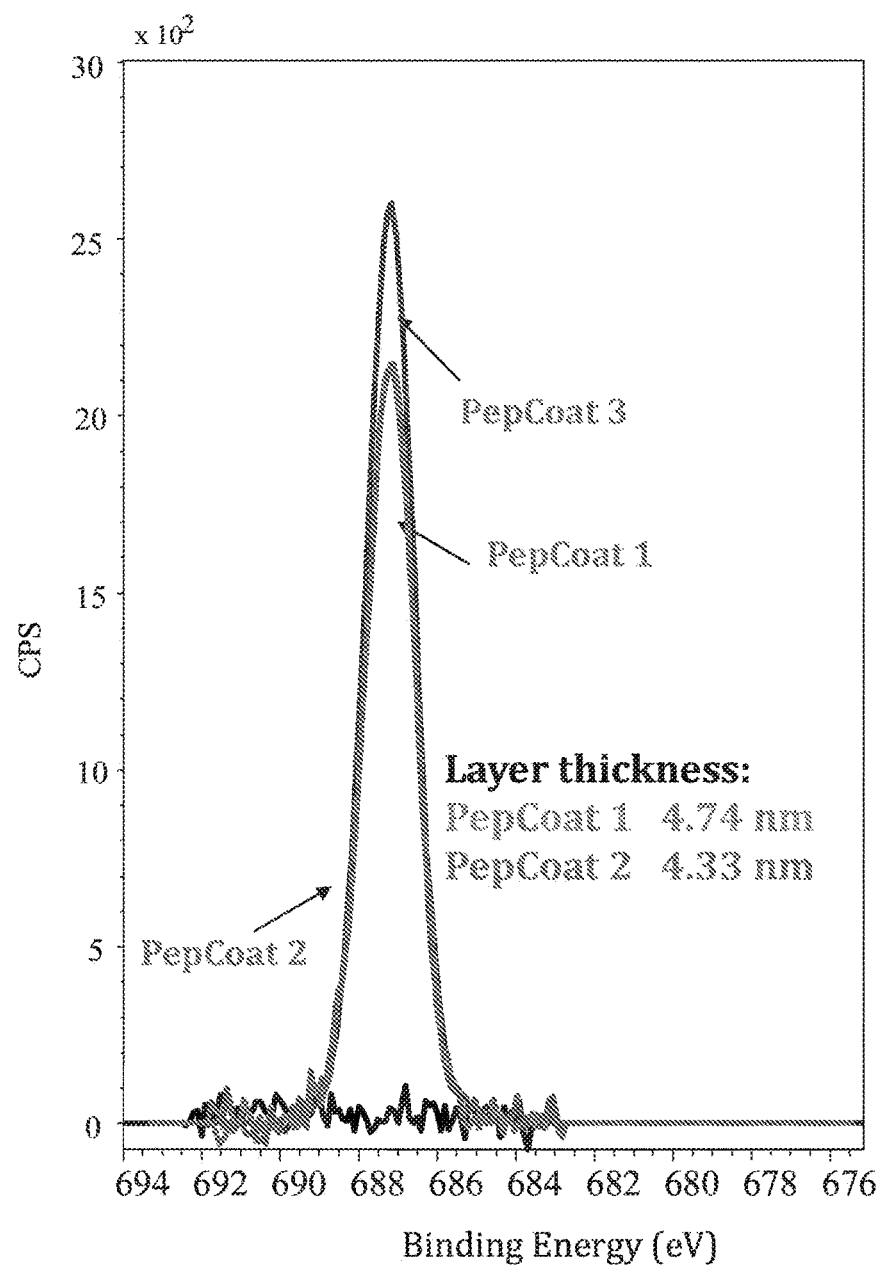
FIG. 3 shows XPS analysis of surfaces coated with compounds of the invention.
Figure 4A:
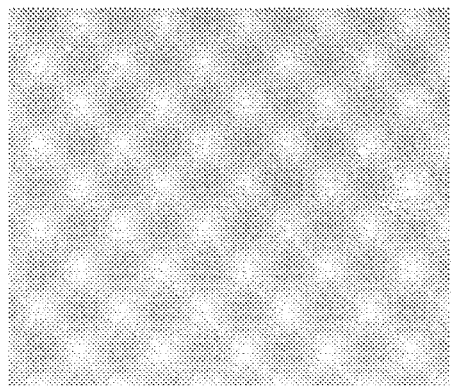
FIGS. 4A-E show SEM images of surfaces coated with compounds of the invention.
Figure 4B:
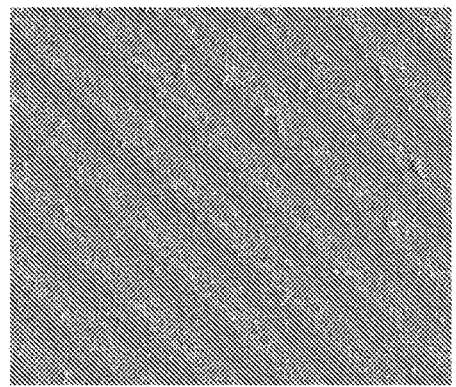
Figure 4C:
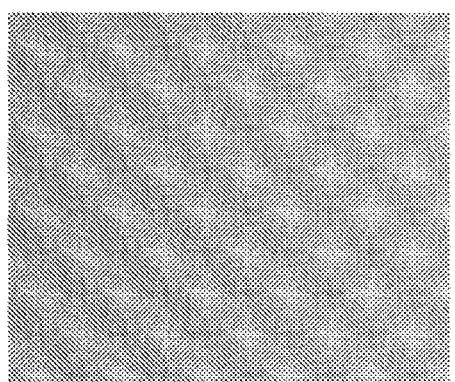
Figure 4D:
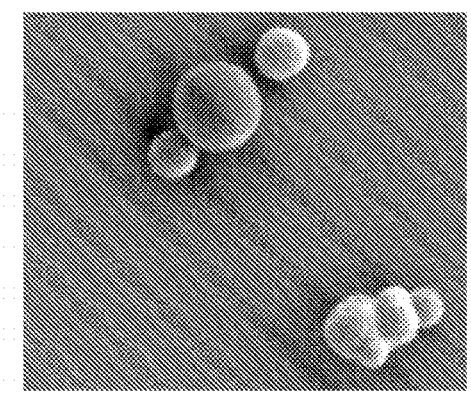
Figure 4E:
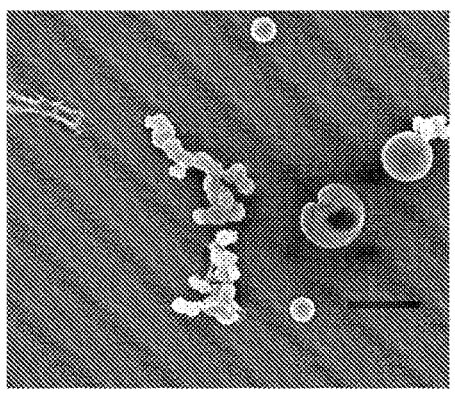
Figure 5A:
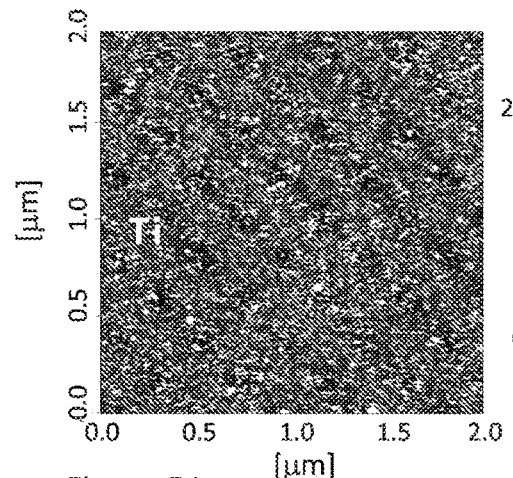
FIGS. 5A-E show AFM images of surfaces coated with compounds of the invention.
Figure 5B:
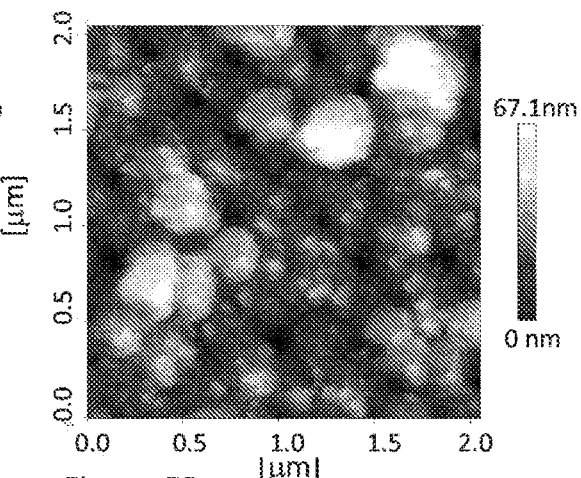
Figure 5C:
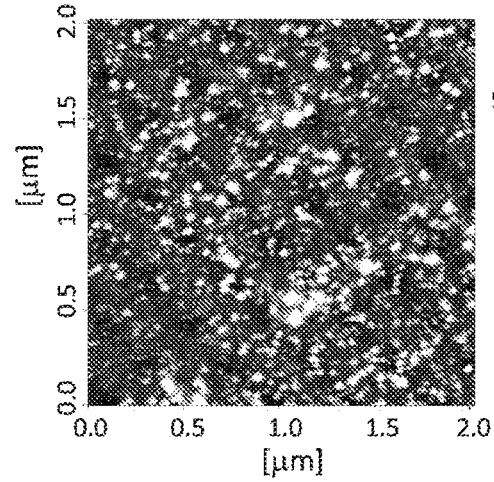
Figure 5D:
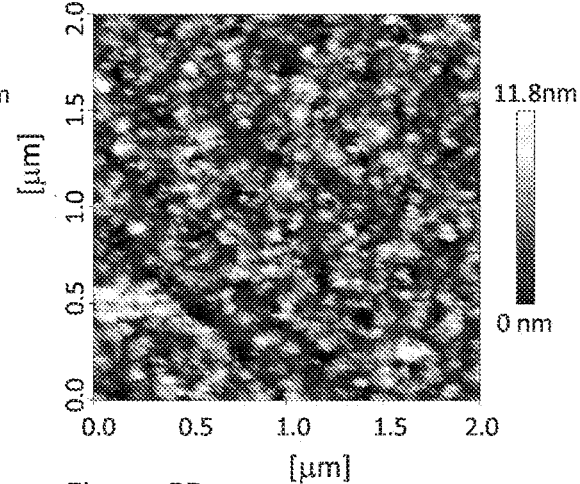
Figure 5E:
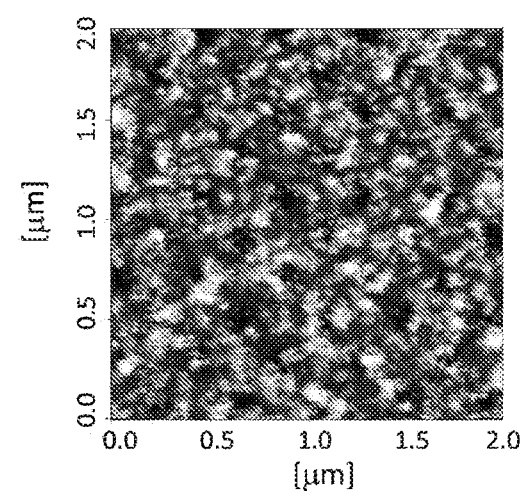

Using X-ray Photoelectron Spectrometry (XPS) analysis, the presence of fluorine atoms on the surface and the thickness of the peptide layer were characterized. As expected, in the case of a bare titanium, there was no indication of the presence of fluorine, while in all cases of substrate-coated with peptides, the presence of fluorine signal indicated the deposition of the peptides on the surface (FIG. 3). The thickness of the peptide layers was also evaluated by the XPS and it was found to be 4.74 nm and 4.33 nm for Peptide 1 and Peptide 2, respectively. For Peptide 3, it was not possible to evaluate the thickness because apparently the organic layer was too thick.

In order to further examine the film formed, Scanning Electron Microscopy (SEM) was utilized. SEM revealed formation of large spherical assemblies in the case of Peptide 3 and Peptide 4 (FIGS. 4A-E). In the case of Peptide 1 and 2, no ordered assemblies were detected. It has, therefore, been assumed that the large assemblies did not allow the estimation of the layer thickness in the case of Peptide 3 by XPS.

For further characterization of the coating topography and thickness, Atomic Force Microscopy (AFM) analysis of Ti surfaces coated with the different peptides was performed. AFM analysis clearly showed (FIGS. 5A-E) that the topography of the Bare Ti was different from the topography of the coated Ti. The topography of Peptides 2-4 looked similar to each other and indicated on a layer having a thickness of 7-10 nm. Peptide 1 showed a different topography with a thicker layer of around 65 nm.

Figure 6A:
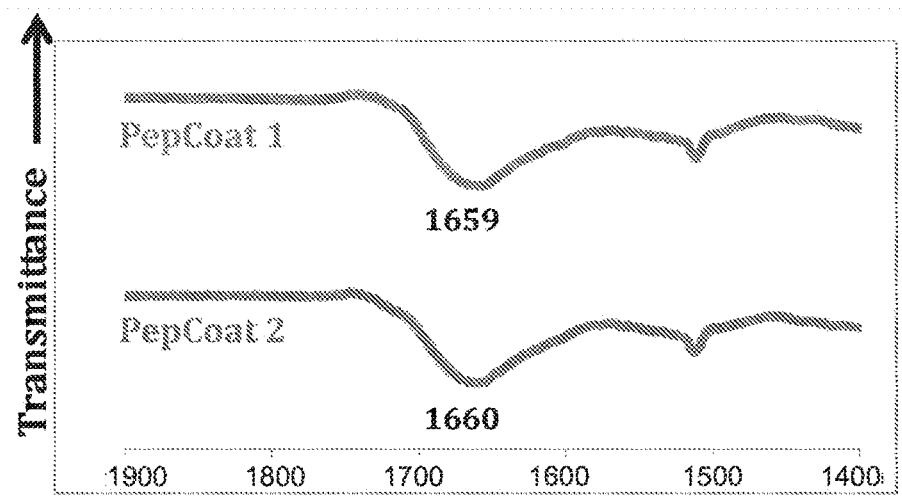
FIGS. 6A-B show FTIR analyses of surfaces coated with Peptides 1 and 2 in comparison to a surface coated with Peptide 3.
Figure 6B:
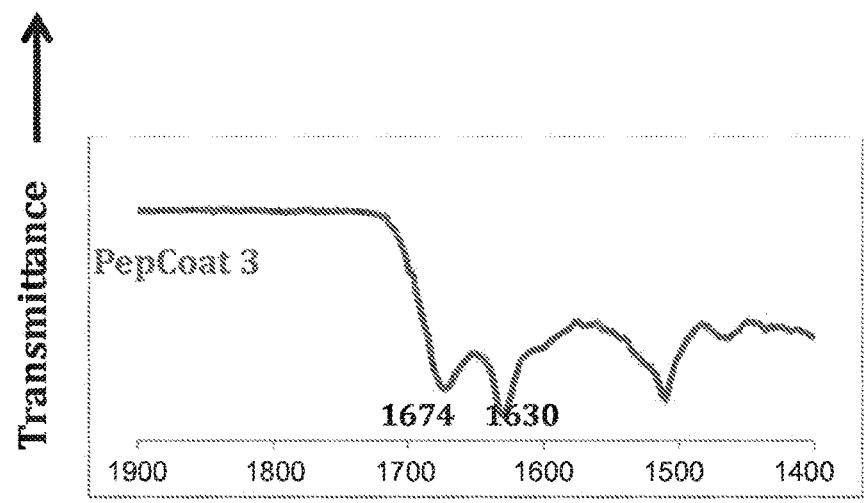

As mentioned before, Peptide 3 formed big spherical assemblies on the surface. For that reason it was not possible to perform ATR-FTIR analysis as no additional peaks were observed in the case of Peptide 3 modified surface compared to titanium surface (FIG. 6A in comparison to FIG. 6B).

Figure 7:
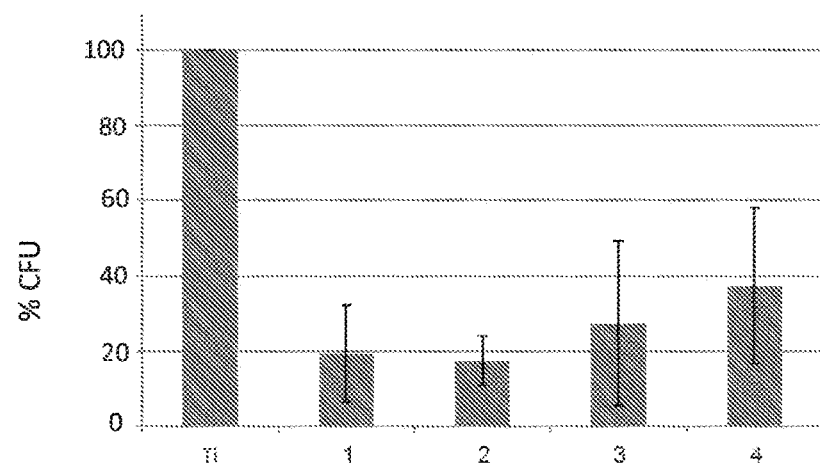
FIG. 7 shows adherence of *Escherichia Coli* to bare and peptide coated substrates.

To assess the bacterial attachment to the surfaces and the anti-fouling activity of the peptides, the adherence of *Escherichia Coli* to bare and peptide coated substrates was promoted. Following this, the surfaces incubated overnight in the bacteria medium to enable the biofilm formation. After the incubation, the surfaces were slowly rinsed, swabbed the adhered bacteria and seeded them in order to evaluate the number of live bacteria on the substrates. The plot in FIG. 7 shows that a better activity was achieved by Peptide 1 and 2 with a reduction of up to 80% and 82%, respectively, as compared to a bare Ti surface. For Peptide 3 and 4 a reduction was also great, being up to 72% and 62%, respectively.

Materials and Methods

All chemicals, solvents, proteins and bacteria were purchased from commercially available companies and used as supplied unless otherwise stated. Fmoc-DOPA(ac)-COOH was obtained from Novabiochem/EMD chemicals (San-Diego, USA). L and D-4-fluoro phenylalanine, Boc-penta Fluoro phe-COOH were purchased from chem-impex Inc. (Wood Dale, USA). Solvents and TFA were purchased from Bio-lab(Jerusalem, Israel). NMR solvents ($CDCl_3$ and $DMSO-d_6$) were supplied by Sigma-Aldrich (Jerusalem, Israel). Piperidine used for deprotection of Fmoc group was obtained from Alfa-Aesar (UK). The proteins BSA, fibrinogen and lysozyme were obtained from Sigma-Aldrich (Jerusalem, Israel), Chem impex INC. (Wood Dale, USA) and Merck (Darmstadt, Germany) respectively. *Pseudomonas aeruginosa* (ATCC 27853) and *Escherichia coli* (ATCC 1655) were purchased from ATCC (Virginia, USA). Crystal violet was obtained from Merck (Germany).

Substrates

Silicon wafers (100) with a diameter of 2 inches were coated with 50 nm titanium (as measured by quartz crystal) by electron beam evaporation (TFDS-141E, VST) at a rate of 1 Å/sec. In the same manner silicon wafers were coated with 15 nm titanium and then 150 nm of gold. The coated wafers were diced (7100 2" Pro-Vectus, ADT) into 1 cm×1 cm pieces.

High Performance Liquid Chromatography (HPLC)

Analytical reversed-phase (RP) HPLC analysis was performed on a Waters Alliance HPLC with UV detection (220 nm and 280 nm) using a XSelect C18 column (3.5 μm, 130 Å, 4.6×150 mm). Preparative RP-HPLC was performed on a Waters 150QLC system using a XSelect C18 column (5 μm, 130 Å, 30×250 mm). Linear gradients of acetonitrile (with 0.1% TFA) in water (with 0.1% TFA) were used for all systems to elute bound peptides. The flow rates were 1 mL/min (analytical, column heated at 30° C.) and 20 mL/min (preparative).

Mass Spectrometry (MS)

Electrospray ionization MS was performed on LCQ Fleet Ion Trap mass spectrometer (Thermo Scientific).

Surface Modification 1 cm×1 cm titanium surfaces were sonicated for 5 minutes in ethanol, washed with TDW and dried under nitrogen. The clean surfaces were dipped in a peptide solution (1 mg/mL in TRIS buffer at pH=8.5, 10 mM concentration and ionic strength of 154 mM with NaCl) and left for incubation overnight at room temperature. Then, the modified substrate were rinsed three times with 1 ml TDW and dried under nitrogen.

Contact Angle Measurements

Contact angle measurements were carried out using a Theta Lite optical tensiometer (Attension, Finland).

ATR-FTIR Analysis

ATR spectra were recorded using FT-IR (Thermo scientific, Model Nicolet 6700) with GeATR arrangement (Harrick Scientific's VariGATR). For all the surfaces spectra were collected with applied force of 350 N, at 4 $cm^{-1}$ resolution with 3000 scans averaged signal and an incident angle of 65°. The transmittance minimal values were determined by the OMNIC analysis program (Nicolet).

FTIR Analysis

Infrared spectra were recorded using a Nicolet 6700 FT-IR spectrometer with a deuterated triglycine sulfate (DTGS) detector (Thermo Fisher Scientific, MA, USA). Peptide solution were deposited on a $CaF_2$ plate and dried by vacuum. The peptide deposits were resuspended with $D_2O$ and subsequently dried to form thin films. The resuspension procedure was repeated twice to ensure maximal hydrogen-to-deuterium exchange. The measurements were taken using a 4 $cm^{-1}$ resolution and averaging 1000 scans. The transmittance minimal values were determined by the OMNIC analysis program (Nicolet).

NMR Analysis

NMR spectra were obtained at 400.13 MHz (1H) using a Bruker DRX 400 spectrometer. The mass of the peptides was measured using Applied Biosystem Voyager-DE pro MALDI TOF mass spectrometer. The peptides were synthesized by a conventional solution-phase method using a racemization free strategy. The Boc group and Fmoc group were used for N-terminal protection and the C-terminus was protected as a methyl ester. Couplings were mediated by dicyclohexylcarbodiimide/1-hydroxybenzotriazole (DCC/ HOBt). The intermediate compounds were characterized by $^1$H NMR and MALDI-TOF mass spectroscopy and final peptides were fully characterized by $^1$H NMR, $^{13}$C NMR, $^{19}$F NMR, MALDI-TOF.

AFM

Surfaces were prepared in the same manner as was mentioned before. AFM images were taken in AC mode with Si tip with spring constant 3 N/m in JPK instrument (NanoWizard 3).

Biofilm Formation

Escherichia coli were grown in LB medium for 5.5 hours at 37° C. in loosely capped erlenmeyer flask with agitation (120 rpm). The $OD_\lambda$=600 nm of the culture was measured using UV-1650PC spectrophotometer (SHIMADZU) to confirm absorbance of ~1.5 uL of the bacteria culture were then seeded onto each substrate (1 cm×1 cm) in 24-well plates and incubated for 75 min at room temperature to allow initial adhesion of the bacteria. Afterward, LB media (2 mL) were added to each well and the plates were incubated at 37° C. overnight.

Quantification of Live Bacteria on the Substrates

Each surface was rinsed by shaking the surface in sterilized water three times. A sterile swab was then used to pick up the biofilms attached to the surfaces. The swabs were inserted into eppendorf tubes containing 1 mL of sterilized water and vortexed for 1 min. Each sample was decimally diluted and plated out on dried LB agar (10 g LB and 7.5 g agar per 0.5 L TDW) plate (8 drops of 10 ul for each dilution). Plate counts (CFU mL-1) were carried out after incubation over night at 37° C. The data presents 3 experiments with triplicates for each experiment. The data is given as mean values ±standard deviations. Significant differences between group means were analyzed by t-test and confidence levels were set at 95%.

Crystal Violet Assay

The substrates were rinsed by shaking the surface in sterilized water three times and stained with 0.2% crystal violet for 30 minutes. The stained samples were washed with running water and left to dry in air. Eventually the bound dye was eluted with 30% acetic acid. Absorbance values were recorded at 590 nm in a microplate reader (Synergy 2, BioTek). All measurements were performed in triplicates and averaged.

Cell Culture

Cellular experiments were performed using the Human Embryonic Kidney (HEK) 293T17 cells. HEK293 cells were cultured in P medium supplemented with 10% (v/v) fetal bovine serum (FBS), 50 U/mL penicillin, and 1% (w/v) L-glutamine. Cells were maintained at 37° C., in a humidified atmosphere containing 5% (v/v) $CO_2$, changing culture medium twice a week. Upon reaching 90% confluence, cells were detached by trypsin and subcultured into a new flask.

Peptide Synthesis

The peptides were synthesized manually by solid phase peptide synthesis (SPPS) on 0.25 mmol scale using rink amide resin. The Fmoc protecting group was removed with solution of 20% piperidine in DMF (15 min×2) and then washed with DMF. The amino acids were activated using DIEA/HATU mixture for 3 minutes. amino acids were used in 5-fold excess, except the (4F)Phe and DOPA that was 2-fold excess. The amount of DIEA and HATU was determined according to the amount of the amino acids (2 and 1 molar equiv. for DIEA and HATU, respectively). The amino acids were allowed to couple for 1.5 hours with constant shacking. The cleavage of the peptide from the resin was done after washing the resin with DMF and DCM and drying under vacuum. The peptide was cleaved using a mixes solution of 30 ml TFA/TDW/TIPS (95:2.5:2.5) for 3 hours. The cleavage solution was evaporated to minimum volume by bubbling nitrogen and the crude peptide product was precipitated with diethyl ether. The precipitated crude peptide was centrifuged and the crude peptide was dissolved in minimum volume of 0.1% TFA in TDW and lyophilized before purification with HPLC.

A. Synthesis of Peptide 5

1. Boc-L-(4F)Phe-COOH 8a: A solution of L-4F-Phe-COOH 1.97 g (10 mmol) in a mixture of dioxane (20 mL), water (20 mL) and 1 M NaOH (10 mL) was stirred and cooled in an ice-water bath. Ditert-butylpyrocarbonate 2.4 g (11 mmol) was added and stirring was continued at room temperature for 6 h. Then the solution was concentrated in vacuum to about 15-20 mL, cooled in an ice water bath, covered with a layer of ethyl acetate (about 30 mL) and a dilute solution of $KHSO_4$ was added to acidify (pH 2-3). The aqueous phase was extracted with ethyl acetate and this operation was done three times. The ethyl acetate extracts were collected and dried over anhydrous $Na_2SO_4$ and evaporated in a vacuum. The pure material was obtained as a waxy solid.

Yield: 2.115 g (7.25 mmol, 72.5%)

$^1$H NMR (DMSO-d6, 400 MHz, 6 ppm): 12.60 [s, 1H COOH], 7.29-7.25 & 7.11-7.07 [m, 4H, Aromatic protons], 4.10-3.00 [m, 1H, CuH 4F Phe], 3.03-2.77 [m, 2H, COH 4F Phe], 1.33 [s, 9H, Boc].

MALDI-TOF (matrix:α-cyano-4-hydroxy cinnamic acid (CHCA)):m/z=[M+H]+ 284.12 (calculated), 284.29 (observed), [M+Na]+306.11 (calculated), 306.25 (observed).

2. Boc-L-(4F)Phe(2)-L-(4F)Phe(3)-COOMe 9a: 500 mg (1.766 mmol) of Boc-L-(4F)Phe-OH was dissolved in 25 mL dry DCM in an ice-water bath. $NH_2$-L-(4F)Phe-OMe 697.13 mg (3.532 mmol) was isolated from the corresponding methyl ester hydrochloride by neutralization, subsequent extraction with ethyl acetate and solvent evaporation. It was then added to the reaction mixture, followed immediately by 365 mg (1.766 mmol) dicyclohexylcarbodiimide (DCC) and 239 mg (1.766 mmol) of HOBt. The reaction mixture was allowed to come to room temperature and stirred for 48 h. DCM was evaporated and the residue was dissolved in ethyl acetate (60 mL) and dicyclohexyl urea (DCU) was filtered off. The organic layer was washed with 2 M HCl (3×30 mL), brine (2×30 mL), 1 M sodium carbonate (3×30 mL) and brine (2×30 mL) and dried over anhydrous sodium sulfate; and evaporated in a vacuum to yield compound 8a, as a white solid. The product was purified by silica gel (100-200 mesh) using n hexane-ethyl acetate (4:1) as eluent.

Yield: 616.6 mg (1.334 mmol, 75.5%)

$^1$H NMR (CDCl3, 400 MHz, 6 ppm): 7.16-7.12 & 6.99-6.90 [m, 8H, Aromatic protons], 6.27-6.25 [d, 1H, NH 4F Phe(3)], 4.93 [b, 1H, NH 4F Phe(2)], 4.77-4.72 [m, 1H, CαH 4F Phe(3)], 4.28-4.27 [m, 1H, CuH 4F Phe(2)], 3.67 [s, 3H, OMe], 3.08-2.98 [m, 4H, CβH 4F Phe(2) and 4F Phe(3)], 1.41 [s, 9H, Boc].

MALDI-TOF (matrix:α-cyano-4-hydroxy cinnamic acid (CHCA)):m/z=[M+Na]+485.18 (calculated), 485.45 (observed), [M+K]+501.16 (calculated), 501.32 (observed).

3. $NH_2$-L-(4F)Phe(2)-L-(4F)Phe(3)-COOMe 10a: 600 mg (1.298 mmol) compound 8a was dissolved in 16 mL of DCM in an ice bath. Then 4 ml of TFA was added and stirred for 2 h. The progress of reaction was monitored through TLC (Thin layer chromatography). After completion of reaction all the solvents were evaporated in rotary evaporator. The product was dissolved in water, neutralized with NaHCO$_3$ solution and extracted with ethyl acetate, dried over anhydrous sodium sulphate, evaporated into rotary evaporator to get oily product 10a.

Yield: 435.3 mg (1.202 mmol, 92.6%)

$^1$H NMR (DMSO-d$_6$, 400 MHz, δppm): 9.06-9.05 [d, 1H, NH 4F Phe(3)], 7.32-7.26 & 7.17-7.04 [in, 8H, Aromatic protons], 4.57-4.51 [m, 1H, CαH 4F Phe(3)], 4.04-3.96 [m, 1H, CαH 4F Phe(2)], 3.61 [s, 3H, OMe], 3.18-2.91 [m, 4H, CβH 4F Phe(2) and 4F Phe(3)].

MALDI-TOF (matrix:α-cyano-4-hydroxy cinnamic acid (CHCA)):m/z=[M+2H]+364.14 (calculated), 364.34 (observed), [M+H$_2$O]+480.15 (calculated), 480.35 (observed).

4. Fmoc-L-DOPA(ac)-L-(4F)Phe(2)-L-(4F)Phe(3)-COOMe 11a: 430 mg (1.187 mmol) of compound 10a was dissolved in 25 mL dry DCM in an ice-water bath and 652.37 mg (1.42 mmol) of Fmoc-L-DOPA(ac)-COOH was added. Then 245 mg (1.187 mmol) dicyclohexylcarbodiimide (DCC) and 161 mg (1.187 mmol) of HOBt were added to reaction mixture. The reaction mixture was allowed to come to room temperature and stirred for 48 h. DCM was evaporated and the residue was dissolved in ethyl acetate (60 mL) and dicyclohexylurea (DCU) was filtered off. The organic layer was washed with water, extracted, dried over anhydrous sodium sulfate and evaporated in a vacuum to yield compound 11a, as a white solid. The product was purified by silica gel (100-200 mesh) using n hexane-ethyl acetate (4:1) as eluent.

Yield: 594.8 mg (0.74 mmol, 62.4%).

$^1$H NMR (CDCl$_3$, 400 MHz, δ$_{ppm}$): 7.77-7.75, 7.54-7.50, 7.42-7.38, 7.33-7.29 [d & m, 8H, Fmoc aromatic protons], 7.05-6.86 [m, 8H, 4F Phe(2) and 4F Phe(3) aromatic protons], 6.62-6.55 [s & m, 3H, DOPA aromatic protons], 6.50 [b, 1H, NH 4F Phe(2)], 6.19 [b, 1H, NH 4F Phe(3)], 5.17 [b, 1H, NH DOPA], 4.68-4.66 [m, 1H, CαH DOPA], 4.54-4.52 [m, 1H, CuH 4F Phe(2)], 4.47-4.42 [m, 1H, CαH 4F Phe(3)], 4.31 (b, 2H, COH Fmoc), 4.20-4.17 [m, 1H, CαH Fmoc], 3.65 [s, 3H, OMe], 2.98-2.92 [m, 6H, CβH 4F Phe(2) 4F Phe(3) & DOPA], 1.62 [s, 6H, 2×COCH$_3$].

MALDI-TOF (matrix:α-cyano-4-hydroxy cinnamic acid (CHCA)):m/z=[M+H]+ 804.31 (calculated), 804.70 (observed), [M+Na+2H]$^+$828.30 (calculated), 828.07 (observed), [M+K+H]$^+$843.27 (calculated), 843.60 (observed).

5. NH$_2$-L-DOPA(ac)-L-(4F)Phe(2)-L-(4F)Phe(3)-COOMe 12a: 580 mg (0.721 mmol) of compound 11a was treated 15 mL with 20% piperidine solution and stirred for 3 h in room temperature. The completion of reaction was monitored by TLC. Then the solution was lyophilized and purified with column chromatography to get pure sticky compound 12a.

Yield: 275.6 mg (0.474 mmol, 65.8%)

$^1$H NMR (DMSO-d$_6$, 400 MHz, δ$_{ppm}$): 8.53 [b, 1H, NH 4F Phe(2)], 7.96 [b, 1H, NH 4F Phe(3)], 7.24-7.23, 7.10-7.04 [m, 8H, 4F Phe(2) and 4F Phe(3) aromatic protons], 6.69-6.65, 6.55-6.53 [m, 3H, DOPA aromatic protons], 5.56 [m, 1H, CuH DOPA], 4.56 [m, 1H, CαH 4F Phe(2)], 4.47 [m, 1H, 4F Phe(3)], 3.61 [s, 3H, OMe], 3.12-2.73 [m, 6H, CβH 4F Phe(2) 4F Phe(3) & DOPA], 1.61-1.58 [d, 6H, 2×COCH$_3$].

MALDI-TOF (matrix:α-cyano-4-hydroxy cinnamic acid (CHCA)):m/z=[M+H]$^+$ 582.23 (calculated), 582.25 (observed), [M+Na]$^+$604.22 (calculated), 604.37 (observed), [M+K]$^+$620.20 (calculated), 620.19 (observed).

6. NH$_2$-L-DOPA-L(4F)-Phe(2)-L(4F)-Phe(3)-COOMe 5:260 mg (0.447 mmol) of compound 12a, was stirred in 10 mL of 95% TFA in water for 6 h. The progress of the reaction was monitored through TLC. After completion of reaction the solvent was evaporated in rotary evaporator. The product was washed with hexane, cold ether and water three times each to get final Peptide 5.

Yield: 139.1 mg (0.257 mmol, 57.5%)

$^1$H NMR (DMSO-d$_6$, 500 MHz, δ$_{ppm}$): 8.72-8.70 [d, 1H, NH 4F Phe(2)], 8.66-8.64 [d, 1H, NH 4F Phe(3)], 7.88 [b, 2H, OH DOPA], 7.29-7.23, 7.12-7.05 [m, 8H, 4F Phe(2) and 4F Phe(3) aromatic protons], 6.7-6.64, 6.5-6.47 [m, 3H, DOPA aromatic protons], 4.60-4.58 [m, 1H, CuH 4F Phe (2)], 4.53-4.52 [m, 1H, CuH 4F Phe(3)], 3.83 [m, 1H, CαH DOPA], 3.58 [s, 3H, OMe], 3.08-2.75 [m, 6H, CβH 4F Phe(2) 4F Phe(3) & DOPA]. $^{13}$C NMR (DMSO-d$_6$, 125 MHz, δ$_{ppm}$): 171.9, 170.1, 168.5, 158.9, 158.54, 145.2, 144.5, 131.5, 125.2, 117.4, 115.5, 115.4, 115.3, 11.2, 114.5, 53.9, 52.3, 47.5, 36.2, 33.8, 25.8, 24.9. $^{19}$F NMR (DMSO-d$_6$, 470 MHz, δ$_{ppm}$): −116.42, −116.71.

MALDI-TOF (matrix:α-cyano-4-hydroxy cinnamic acid (CHCA)):m/z=[M+H]$^+$ 542.20 (calculated), 542.57 (observed), [M+Na]$^+$564.19 (calculated), 564.46 (observed), [M+K]$^+$580.16 (calculated), 580.32 (observed).

B. Synthesis of Peptide 6

1. Boc-L-(4F)Phe(2)-D-(4F)Phe(3)-COOMe 9b: The compound was synthesized with the same procedure as compound 9a.

$^1$H NMR (CDCl$_3$, 400 MHz, δ$_{ppm}$): 7.13-7.10 & 6.98-6.91 [m, 8H, Aromatic protons], 6.51 [b, 1H, NH 4F Phe(3)], 4.91-4.89 [d, 1H, NH 4F Phe(2)], 4.82-4.77 [m, 1H, CαH 4F Phe(3)], 4.33 [m, 1H, CuH 4F Phe(1)], 3.68 [s, 3H, OMe], 3.09-2.93 [m, 4H, COH 4F Phe(2) and 4F Phe(3)], 1.38 [s, 9H, Boc].

MALDI-TOF (matrix:α-cyano-4-hydroxy cinnamic acid (CHCA)):m/z=[M+2H]$^+$464.21 (calculated), 464.15 (observed), [M+Na+2H]$^+$586.18 (calculated), 586.37, [M+K+H]$^+$502.16 (calculated), 502.25 (observed).

2. NH$_2$-L-(4F)Phe(2)-D-(4F)Phe(3)-COOMe 10b: The compound was synthesized with the same procedure as compound 10a.

$^1$H NMR (DMSO-d$_6$, 400 MHz, δ$_{ppm}$): 8.34 [d, 1H, NH 4F Phe(3)], 7.23-7.19 & 7.12-7.01 [m, 8H, Aromatic protons], 4.61-4.51 [m, 1H, CαH 4F Phe(3)], 3.62 [s, 3H, OMe], 3.44-3.41 [m, 1H, CuH 4F Phe(2)], 3.03-2.74 [m, 4H, CβH 4F Phe(2) and 4F Phe(3)]. 2.35 (b, 2H, free NH$_2$].

MALDI-TOF (matrix:α-cyano-4-hydroxy cinnamic acid (CHCA)):m/z=[M+2H]$^+$364.14 (calculated), 364.41 (observed).

3. Fmoc-L-DOPA(ac)-L-(4F)Phe(2)-D-(4F)Phe(3)-COOMe 11b: The compound was synthesized with the same procedure as compound 11a.

$^1$H NMR (DMSO-d$_6$, 400 MHz, δ$_{ppm}$): 8.68-8.55 [d, 1H, NH Phe(2)], 8.15-7.92 [d, 1H, NH 4F Phe(3)], 7.88-7.86, 7.61-6.96 [d & m, 16H, Fmoc aromatic protons, 4F Phe(2) and 4F Phe(3) aromatic protons], 6.75 & 6.64 [s, 3H, DOPA aromatic protons], 5.83 [d, 1H, NH DOPA], 4.62-4.53 [m, 2H, CuH 4F Phe(2) and Phe(3)], 4.14-4.02 [m, 3H, CαH DOPA & COH Fmoc], 3.63 [s, 3H, OMe], 2.76-2.57 [m, 6H, CβH 4F Phe(2), 4F Phe(3) & DOPA], 1.55 [s, 6H, 2×COCH$_3$].

MALDI-TOF (matrix:α-cyano-4-hydroxy cinnamic acid (CHCA)):m/z=[M+Na]$^+$826.29 (calculated), 826.15 (observed), [M+K]$^+$842.27 (calculated), 841.94 (observed).

4. NH$_2$-L-DOPA(ac)-L-(4F)Phe(2)-D-(4F)Phe(3)-COOMe 12b: The compound was synthesized with the same procedure as compound 12a.

$^1$H NMR (DMSO-d$_6$, 400 MHz, δ$_{ppm}$): 8.66-8.64 [b, 1H, NH 4F Phe(2)], 7.95 [b, 1H, NH 4F Phe(3)], 7.30-6.80 [m, 8H, 4F Phe(2) and 4F Phe(3) aromatic protons], 6.68-6.64, 6.56-6.53 [m, 3H, DOPA aromatic protons], 5.57-5.55 [m, 1H, CαH DOPA], 4.56 [m, 1H, CαH 4F Phe(2)], 4.47 [m, 1H, 4F Phe(3)], 3.63 [s, 3H, OMe], 3.05-2.67 [m, 6H, CβH 4F Phe(2), 4F Phe(3) & DOPA]. 1.59-1.57 [s, 6H, 2×COCH$_3$].

MALDI-TOF (matrix:α-cyano-4-hydroxy cinnamic acid (CHCA)): m/z=[M+Na]$^+$604.22 (calculated), 604.06 (observed), [M+K]$^+$620.20 (calculated), 619.88 (observed).

5. NH$_2$-L-DOPA-L-(4F)Phe(2)-D-(4F)Phe(3)-COOMe 6: The Peptide 6 was synthesized with the same procedure as Peptide 5.

$^1$H NMR (DMSO-d$_6$, 500 MHz, δ$_{ppm}$): 8.77-8.75 [d, 1H, NH 4F Phe(2)], 8.66-8.64 [d, 1H, NH 4F Phe(3)], 7.80 [b, 2H, OH DOPA], 7.27-7.24, 7.11-7.00 [m, 8H, 4F Phe(2) and 4F Phe(3) aromatic protons], 6.71-6.60 [m, 3H, DOPA aromatic protons], 5.15 [b, 2H, NH$_{2]}$, $_{4.62}$-4.60 [m, 1H, CαH 4F Phe(2)], 4.52-4.49 [m, 1H, CαH 4F Phe(3)], 3.83 [m, 1H, CαH DOPA], 3.65 [s, 3H, OMe], 3.10-2.73 [m, 6H, CβH 4F Phe(2), 4F Phe(3) & DOPA]. $^{13}$C NMR (DMSO-d$_6$,125 MHz, δ$_{ppm}$): 117.43, 170.42, 147.86, 146.63, 143.75, 143.69, 141.30, 135.47, 128.64, 127.75, 127.23, 127.13, 125.054, 121.81, 120.02, 118.04, 109.44, 108.25, 67.20, 53.02, 52.33, 47.09, 37.91, 31.94, 29.71, 25.89.

$^{19}$F NMR (DMSO-d$_6$, 470 MHz, δ$_{ppm}$): −116.43, −116.91.

MALDI-TOF (matrix:α-cyano-4-hydroxy cinnamic acid (CHCA)):m/z=[M+H]$^+$ 542.20 (calculated), 542.65 (observed), [M+Na]$^+$564.19 (calculated), 564.55 (observed), [M+K]$^+$580.16 (calculated), 580.57 (observed).

C. Synthesis of Peptide 7

1. Boc-D-(4F)Phe-COOH 13b: The compound 13b was synthesized as compound 13a.

$^1$H NMR (DMSO-d$_6$, 400 MHz, δ$_{ppm}$): 12.59 [s, 1H COOH], 7.29-7.26 & 7.12-7.08 [m, 4H, Aromatic protons], 4.10-3.57 [m, 1H, CαH 4F Phe], 3.03-2.77 [m, 2H, CβH 4F Phe], 1.32 [s, 9H, Boc].

MALDI-TOF (matrix:α-cyano-4-hydroxy cinnamic acid (CHCA)):m/z=[M+H]$^+$ 284.12 (calculated), 284.36 (observed), [M+Na]$^+$306.11 (calculated), 306.28 (observed).

2. Boc-D-(4F)Phe(2)-L-(4F)Phe(3)-COOMe 9c: The compound was synthesized with the same procedure as compound 9a.

$^1$H NMR (CDCl$_3$, 400 MHz, δ$_{ppm}$): 7.14-7.09 & 6.99-6.93 [m, 8H, Aromatic protons], 6.50 [b, 1H, NH 4F Phe(3)], 4.88 [b, 1H, NH 4F Phe(2)], 4.82-4.77 [m, 1H, CαH 4F Phe(3)], 4.33 [m, 1H, CαH 4F Phe(2)], 3.68 [s, 3H, OMe], 3.09-2.91 [m, 4H, CβH 4F Phe(2) and 4F Phe(3)], 1.38 [s, 9H, Boc].

MALDI-TOF (matrix:α-cyano-4-hydroxy cinnamic acid (CHCA)):m/z=[M+Na]$^+$485.18 (calculated), 485.88 (observed), [M+K]$^+$501.16 (calculated), 501.75 (observed).

3. NH$_2$-D-(4F)Phe(2)-L-(4F)Phe(3)-COOMe 10c: The compound was synthesized with the same procedure as compound 10a.

$^1$H NMR (DMSO-d$_6$, 400 MHz, δ$_{ppm}$): 8.71-8.67 [d, 1H, NH 4F Phe(3)], 7.25-7.21 & 7.12-7.03 [in, 8H, Aromatic protons], 5.49 [b, 2H, NH$_2$], 4.56-4.54 [m, 1H, CαH 4F Phe(2)], 3.77-3.70[m, 1H, CαH 4F Phe(3)], 3.64 [s, 3H, OMe] 3.07-2.57 [m, 4H, CβH 4F Phe(2) and 4F Phe(3)].

MALDI-TOF (matrix:α-cyano-4-hydroxy cinnamic acid (CHCA)):m/z=[M+2H]$^+$364.14 (calculated), 364.26 (observed).

4. Fmoc-L-DOPA(ac)-D-(4F)Phe(2)-L-(4F)Phe(3)-COOMe tic: The compound was synthesized with the same procedure as compound 11a.

$^1$H NMR (CDCl$_3$, 400 MHz, δ$_{ppm}$): 7.79-7.72, 7.51-7.47, 7.42-7.38, 7.33-7.29 [d & m, 8H, Fmoc aromatic protons], 6.94-6.88 [m, 8H, 4F Phe(2) and 4F Phe(3) aromatic protons], 6.76-6.61[s & m, 3H, DOPA aromatic protons], 6.54 [b, 1H, NH 4F Phe(2)], 6.18 [b, 1H, NH 4F Phe(3)], 5.20 [b, 1H, NH DOPA], 4.76-4.68 [m, 1H, CαH DOPA], 4.67-4.57 [m, 1H, CαH 4F Phe(2)], 4.43-4.35 [m, 1H, CαH 4F Phe(3)],], 4.30-4.21 [m, 1H, CαH Fmoc], 4.19-4.01 (b, 2H, COH Fmoc], 3.62 [s, 3H, OMe], 3.09-2.75 [m, 6H, CβH 4F Phe(2), 4F Phe(3) & DOPA], 1.63 [s, 6H, 2×COCH$_3$].

MALDI-TOF (matrix:α-cyano-4-hydroxy cinnamic acid (CHCA)):m/z=[M+H]$^+$ 804.31 (calculated), 804.74 (observed), [M+Na+H]$^+$827.30 (calculated), 827.32 (observed), [M+K+H]$^+$843.27 (calculated), 843.62 (observed).

5. NH$_2$-L-DOPA(ac)-D-(4F)Phe(2)-L-(4F)Phe(3)-COOMe 12c: The compound was synthesized with the same procedure as compound 12a.

$^1$H NMR (DMSO-d$_6$, 400 MHz, δ$_{ppm}$): 8.66-8.64 [b, 1H, NH 4F Phe(2)], 7.95 [b, 1H, NH 4F Phe(3)], 7.29-6.81 [m, 8H, 4F Phe(2) and 4F Phe(3) aromatic protons], 6.68-6.64, 6.54-6.53 [m, 3H, DOPA aromatic protons], 5.57-5.55 [m, 1H, CαH DOPA], 4.60 [m, 1H, CαH 4F Phe(2)], 4.48 [m, 1H, 4F Phe(3)], 3.63 [s, 3H, OMe], 2.88-2.73 [m, 6H, CβH 4F Phe(2), 4F Phe(3) & DOPA]. 1.59-1.56 [s, 6H, 2×COCH$_3$].

MALDI-TOF (matrix:α-cyano-4-hydroxy cinnamic acid (CHCA)):m/z=[M+H]$^+$ 582.23 (calculated), 581.93 (observed), [M+Na]$^+$604.22 (calculated), 604.01 (observed), [M+K]$^+$620.20 (calculated), 619.85(observed).

6. NH$_2$-L-DOPA-D-(4F)Phe(2)-L-(4F)Phe(3)-COOMe 7: The Peptide 7 was synthesized with the same procedure as Peptide 5.

$^1$H NMR (DMSO-d$_6$, 500 MHz, δ$_{ppm}$): 8.72-8.71 [d, 1H, NH 4F Phe(2)], 8.65-8.64 [d, 1H, NH 4F Phe(3)], 7.89 [b, 2H, OH DOPA], 7.28-7.23, 7.12-7.06 [m, 8H, 4F Phe(2) and 4F Phe(3) aromatic protons], 6.67-6.64, 6.49-6.47 [m, 3H, DOPA aromatic protons], 4.61-4.50 [m, 1H, CαH 4F Phe (2)& Phe(3)], 3.85-3.80 [m, 1H, CαH DOPA], 3.58 [s, 3H, OMe], 3.05-2.72 [m, 6H, CβH 4F Phe(2), 4F Phe(3) & DOPA]. $^{13}$C NMR (DMSO-d$_6$, 125 MHz, δ$_{ppm}$): 171.9, 170.9, 168.6, 162.5, 160.6, 158.5, 158.23, 145.7, 145.1, 133.8, 133.7, 133.5, 131.5, 125.8, 120.7, 117.3, 116.1, 115.5, 115.4, 115.3, 115.2, 54.3, 53.9, 52.4, 46.2, 37.3, 37.0, 36.2, 26.7, 25.3, 24.7.

$^{19}$F NMR (DMSO-d$_6$, 470 MHz, δ$_{ppm}$): −116.31, −116.53.

MALDI-TOF (matrix:α-cyano-4-hydroxy cinnamic acid (CHCA)):m/z=[M+H]$^+$ 542.20 (calculated), 542.51 (observed), [M+Na]$^+$564.19 (calculated), 564.53 (observed), [M+K]$^+$580.16 (calculated), 580.43(observed).

D. Synthesis of Peptide 8

1. Boc-D-(4F)Phe(2)-D-(4F)Phe(3)-COOMe 9d: The compound was synthesized with the same procedure as compound 9a.

1H NMR (CDCl3, 400 MHz, 6 ppm): 7.18-7.15 & 7.01-6.925 [m, 8H, Aromatic protons], 6.25-6.23 [d, 1H, NH 4F Phe(3)], 4.93 [b, 1H, NH 4F Phe(2)], 4.77-4.73 [m, 1H, CαH 4F Phe(2)], 4.30-4.28 [m, 1H, CαH 4F Phe(3)], 3.7 [s, 3H, OMe], 3.10-3.00 [m, 4H, CβH 4F Phe(2) and 4F Phe(3)], 1.40 [s, 9H, Boc].

MALDI-TOF (matrix:α-cyano-4-hydroxy cinnamic acid (CHCA)):m/z=[M+Na+H]⁺486.18 (calculated), 485.93 (observed), [M+K+H]⁺502.16 (calculated), 502.00 (observed).

2. NH₂-D-(4F)Phe(2)-D-(4F)Phe(3)-COOMe 10d: The compound was synthesized with the same procedure as compound 10a.

¹H NMR (DMSO-d6, 400 MHz, δ ppm): 8.36-8.34 [d, 1H, NH 4F Phe(3)], 8.02 [b, 1H, NH 4F Phe(2)], 7.22-7.17 & 7.11-7.01 [m, 8H, aromatic protons], 4.55-4.50 [m, 1H, CαH 4F Phe(3)], 4.08-3.92 [m, 1H, CαH 4F Phe(2)], 3.60 [s, 3H, OMe], 3.04-2.84 [m, 4H, CβH 4F Phe(2) and 4F Phe(3)].

MALDI-TOF (matrix:α-cyano-4-hydroxy cinnamic acid (CHCA)):m/z=[M+2H]⁺364.14 (calculated), 364.29 (observed), [M+Na+H]⁺486.13 (calculated), 486.33 (observed).

3. Fmoc-L-DOPA(ac)-D-(4F)Phe(2)-D-(4F)Phe(3)-COOMe 11d: The compound was synthesized with the same procedure as compound 11a.

¹H NMR (CDCl3, 400 MHz, δ ppm): 7.77-7.75, 7.55-7.53, 7.42-7.40 [d & m, 8H, Fmoc aromatic protons], 6.94-6.55 [m, 8H, 4F Phe(2) and 4F Phe(3) aromatic protons], 6.71-6.52 [m, 3H, DOPA aromatic protons], 6.52-6.45 [b, 1H, NH 4F Phe(2)], 6.15 [b, 1H, NH 4F Phe(3)], 5.31 [b, 1H, NH DOPA], 4.73-4.65 [m, 1H, CαH DOPA], 4.64-4.56 [m, CαH 4F Phe(2)], 4.51-4.42 [m, 1H, CαH 4F Phe(3)], 4.24-4.11 [m, 1H, CαH Fmoc], 4.19 (b, 2H, COH Fmoc), 3.61 [s, 3H, OMe], 3.08-2.72 [m, 6H, CβH 4F Phe(2) 4F Phe(3) & DOPA], 1.62 [s, 6H, 2×COCH3].

MALDI-TOF (matrix:α-cyano-4-hydroxy cinnamic acid (CHCA)):m/z=[M+Na+2H]⁺828.30 (calculated), 828.03 (observed), [M+K+2H]⁺844.27 (calculated), 844.12(observed).

4. NH₂-L-DOPA(ac)-D-(4F)-Phe(2)-D-(4F)-Phe(3)-COOMe 12d: The compound was synthesized with the same procedure as compound 12a.

¹H NMR (DMSO-d6, 400 MHz, δ ppm): 8.58-8.53 [d, 1H, NH 4F Phe(2)], 8.12 [d, 1H, NH 4F Phe(3)], 7.31-7.09 [m, 8H, 4F Phe(2) and 4F Phe(3) aromatic protons], 6.69-6.68, 6.61-6.60 [m, 3H, DOPA aromatic protons], 5.63-5.61 [m, 1H, CαH DOPA], 4.61 [m, 1H, CαH 4F Phe(2)], 4.52 [m, 1H, 4F Phe(3)], 3.64 [s, 3H, OMe], 3.15-2.65 [m, 6H, CβH 4F Phe(2) 4F Phe(3) & DOPA]. 1.54 [d, 6H, 2×COCH₃].

MALDI-TOF (matrix:α-cyano-4-hydroxy cinnamic acid (CHCA)):m/z=[M+Na]⁺604.22 (calculated), 604.23 (observed), [M+K]⁺620.20 (calculated), 620.12(observed).

5. NH₂-L-DOPA-D-(4F)Phe(2)-D-(4F)Phe(3)-COOMe 8: The Peptide 8 was synthesized with the same procedure as Peptide 5.

¹H NMR (DMSO-d6, 500 MHz, δ ppm): 8.80-8.77 [d, 1H, NH 4F Phe(2)], 7.95 [b, 2H, OH DOPA], 7.31-7.20, 7.12-7.03 [m, 8H, 4F Phe(2) and 4F Phe(3) aromatic protons], 6.59-6.57, 6.22-6.20 [m, 3H, DOPA aromatic protons], 5.58 [b, 2H, free NH₂)], 4.75-4.62 [m, 1H, CαH 4F Phe(2)], 4.51-4.45 [m, 1H, CαH 4F Phe(3)], 3.91-3.82 [m, 1H, CαH DOPA], 3.62 [s, 3H, OMe], 3.08-2.62 [m, 6H, CβH 4F Phe(2), 4F Phe(3) & DOPA]. 13C NMR (DMSO-d6, 125 MHz, δ ppm): 172.01, 171.20, 168.27, 162.77, 158.59, 158.27, 157.09, 145.65, 145.02, 133.58, 133.71, 131.46, 131.45, 131.37, 125.74, 120.65, 117.37, 115.95, 115.63, 115.42, 115.31, 115.09, 54.14, 52.44, 47.97, 33.80, 25.78, 24.92. 19F NMR (DMSO-d6, 470 MHz, δ ppm): −116.08, −116.42.

MALDI-TOF (matrix:α-cyano-4-hydroxy cinnamic acid (CHCA)):m/z=[M+H]⁺ 542.20 (calculated), 542.85 (observed), [M+Na]⁺564.19 (calculated), 564.55 (observed), [M+K]⁺580.16 (calculated), 580.40(observed).

E. Synthesis of Peptide 9

1. Boc-L-(F5)Phe(2)-L-(F5)Phe(3)-COOMe 9e.

We have purchased Boc-L-(F5)Phe-COOH. We first deprotected the Boc group by treatment of TFA/DCM, then evaporate all the solvents and esterification of NH2-Phe (F5)-COOH was done by treating with thionyl chloride and methanol. Then the compound 9e was synthesized by coupling of Boc-L-(F5)Phe-COOH with NH₂-L-(F5)Phe-COOMe as described for compound 9a.

¹H NMR (CDCl3, 400 MHz, δ ppm): 6.52 [b, 1H, NH Phe(3)], 4.93 [b, 1H, NH 4F Phe(2)], 4.92-4.85 [m, 1H, CαH Phe(3)], 4.42-4.29 [m, 1H, CαH Phe(2)], 3.81 [s, 3H, OMe], 3.42-2.95 [m, 4H, CβH Phe(2) and Phe(3)], 1.44 [s, 9H, Boc].

MALDI-TOF (matrix:α-cyano-4-hydroxy cinnamic acid (CHCA)):m/z=[M+Na+H]⁺630.11 (calculated), 630.08(observed), [M+K+H]⁺646.08 (calculated), 646.13 (observed).

2. NH₂-L-(F5)Phe(2)-L-(F5)Phe(3)-COOMe 10e.

The compound 9e was prepared as described for compound 10a.

¹H NMR (DMSO-d6, 400 MHz, δ ppm): 8.93-8.90 [d, 1H, NH Phe(3)], 8.40 [b, 1H, free NH₂], 4.72-4.70 [m, 1H, CαH Phe(3)], 3.90 [m, 1H, CαH Phe(2)], 3.61 [s, 3H, OMe], 3.17-2.99 [m, 4H, CβH Phe(2) and Phe(3)].

MALDI-TOF (matrix:α-cyano-4-hydroxy cinnamic acid (CHCA)):m/z=[M+Na+H]⁺530.05 (calculated), 530.16(observed), [M+K+H]⁺546.03 (calculated), 646.53 (observed).

3. Fmoc-DOPA(ac)-L-(F5)Phe(2)-L-(F5)Phe(3)-COOMe 11e.

The compound 11e was prepared as described for compound 11a.

¹H NMR (DMSO-d6, 400 MHz, δ ppm): 8.75-8.72 [d, 1H, NH Phe(2)], 8.36-8.34 [b, 1H, NH Phe(3)], 7.88-7.26 [m, 8H, Fmoc aromatic protons], 6.79-6.67 [m, 3H, DOPA aromatic protons], 5.57-5.55 [b, 1H, NH DOPA], 4.66-4.63 [m, 2H, COH Fmoc], 4.14-4.09 [m, 3H, CαH DOPA, CαH Phe(2), CαH Phe(3)], 3.62 [s, 3H, OMe], 3.05-2.90 [m, 6H, CβH Phe(2), Phe(3) & DOPA], 1.56 [s, 6H, 2×COCH3].

MALDI-TOF (matrix:α-cyano-4-hydroxy cinnamic acid (CHCA)):m/z=[M+Na]⁺970.21 (calculated), 970.22(observed), [M+K]⁺986.19 (calculated), 986.04 (observed).

4. NH₂-DOPA(ac)-L-(F5)Phe(2)-L-(F5)Phe(3)-COOMe 12e

The compound 12e was prepared as described for compound 12a.

1H NMR (DMSO-d6, 400 MHz, δ ppm): 8.73-8.71 [d, 1H, NH Phe(2)], 6.69-6.55 [m, 3H, DOPA aromatic protons], 5.57-5.55 [d, 1H, NH Phe(3)], 4.64-6.63 [m, 1H, CαH DOPA], 4.54 [m, 1H, CαH Phe(2)], 4.13-4.08 [m, 1H, CαH Phe(3)], 3.61 [s, 3H, OMe], 3.15-2.67 [m, 6H, CβH Phe(2), Phe(3) & DOPA], 1.60 [s, 6H, 2×COCH3].

MALDI-TOF (matrix:α-cyano-4-hydroxy cinnamic acid (CHCA)):m/z=[M+Na]⁺748.15 (calculated), 748.23(observed), [M+K]⁺764.12 (calculated), 764.06 (observed).

5. NH₂-DOPA-L-(F5)Phe(2)-L-(F5)Phe(3)-COOMe 9

Peptide 9 was prepared as described for Peptide 5.

¹H NMR (DMSO-d6, 400 MHz, δ ppm): 9.46 [b, 1H, NH Phe(2)], 9.25 [b, 1H, NH Phe(2)], 8.39 [b, 2H, free NH₂), 6.68-6.54 [m, 3H, DOPA aromatic protons], 4.69-4.65 [m, 2H, CαH Phe (1) & Phe(2)], 4.55 [m, 1H, CαH DOPA], 3.61 [s, 3H, OMe], 3.01-2.95 67 [m, 6H, CβH Phe(2) Phe(2) & DOPA]0.13C NMR (DMSO-d6, 100 MHz, δ ppm): 193.6, 158.5, 158.2, 144.3, 140.8, 139.5, 133.7, 129.9, 128.5, 127.8, 124.4, 53.8, 44.2, 33.8, 30.5, 29.4, 22.6, 17.6. 19F (DMSO-d6, 470 MHz, δ ppm): −141.7, −142.4, −157.6, −163.1, −163.4.

MALDI-TOF (matrix:α-cyano-4-hydroxy cinnamic acid (CHCA)):m/z=[M+Na]$^+$748.15 (calculated), 748.23(observed), [M+K]$^+$764.12 (calculated), 764.06 (observed).

F. Synthesis of Peptide 7

1. Boc-L-DOPA-COOH:

The compound was synthesized as compound 13a.

$^1$H NMR (DMSO-d6, 400 MHz, δ ppm): 9.13 (b, 2H, 2×OH), 7.35-7.33 [d, 1H, NH DOPA], 7.03-6.88[m, 3H, DOPA aromatic protons], 4.45-4.37 [m, 1H, CαH DOPA], 3.22-2.92 [m, 1H, COH DOPA], 1.75 [s, 9H, OMe].

MALDI-TOF (matrix:α-cyano-4-hydroxy cinnamic acid (CHCA)):m/z=[M+Na]$^+$320.11(calculated), 320.51(observed), [M+K]$^+$336.08 (calculated), 336.29 (observed).

2. Boc-L-DOPA-L-(4F) Phe-COOMe:

The compound was synthesized as compound 9a.

1H NMR (CDCl3, 400 MHz, δ ppm): 7.26-7.24 [d, 1H, NH Phe], 6.90-6.50 [m, 7H, all aromatic protons], 5.24 [b, 1H, NH DOPA], 4.82-4.77 [m, 1H, CαH DOPA], 4.36 [b, 1H, CαH Phe], 3.64 [s, 3H, OMe], 2.99-2.87 [m, 4H, COH DOPA & Phe], 1.42 [s, 9H, Boc].

MALDI-TOF (matrix:α-cyano-4-hydroxy cinnamic acid (CHCA)):m/z=[M+Na+H]$^+$500.18 (calculated), 500.02(observed), [M+K+H]$^+$516.16 (calculated), 516.24 (observed).

3. NH$_2$-L-DOPA-L-(4F) Phe-COOMe 6:

This compound was synthesized as described for 10a.

1H NMR (DMSO-d6, 400 MHz, δ ppm): 8.92 & 8.81 [s, 2H, 2×OH], 8.02 [b, 2H, free NH$_{2]}$, $_{7.27}$-7.09 [m, 4H, aromatic proton Phe], 6.67-6.48 [m, 3H, aromatic protons DOPA], 4.58-4.52 [m, 1H, CαH DOPA], 3.90-3.86 [b, 1H, CαH Phe], 3.61 [s, 3H, OMe], 3.08-2.67 [m, 4H, COH DOPA & Phe]. 13C NMR (DMSO-d6, 100 MHz, δ ppm): 171.4, 168.7, 162.7, 160.4, 158.5, 145.6, 145.0, 133.3, 133.2, 131.4, 125.6, 120.6, 117.2, 115.9, 115.5, 115.3, 54.1, 53.9, 52.4, 41.0, 36.8, 36.2, 23.6.]. 19F NMR(DMSO-d6, 470 MHz, δ ppm): –(116.25-116.29).

MALDI-TOF (matrix:α-cyano-4-hydroxy cinnamic acid (CHCA)):m/z=[M+H]377.15 (calculated), 377.25 (observed), [M+Na]$^+$399.13 (calculated), 399.24(observed).

Another two exemplary peptide derivatives have been synthesized using solid or solution phase synthesis. The purity and identify of the peptides was determined using HPLC and MS spectrometer.

---

The invention claimed is:

1. A compound comprising:
   at least one antifouling moiety to fouling caused by unicellular organisms,
   at least one surface-adsorbing moiety, and
   at least one amino acid sequence promoting adherence of cells of multicellular organisms,
   wherein the at least one antifouling moiety is a fluorine (—F) atom or a group comprising at least one fluorine atom; said at least one surface-adsorbing moiety is selected from the group consisting of 3,4-dihydroxy-L-phenylalanine (DOPA), a DOPA containing moiety and dopamine; and
   wherein said at least one amino acid sequence promoting adherence of cells comprises the amino acid sequence selected from RGD; VRN; and SEQ ID NO: 1-13.

2. The compound according to claim 1, wherein the at least one antifouling moiety comprises between 1 and 20 fluorine atoms.

3. The compound according to claim 1, wherein the at least one antifouling moiety is a fluorinated carbon group.

4. The compound according to claim 3, wherein the fluorinated carbon group is a substituted or unsubstituted alkyl group, substituted or unsubstituted alkenyl group or substituted or unsubstituted alkynyl group.

5. The compound according to claim 3, wherein the fluorinated carbon group is a $C_1$-$C_{20}$ group comprising between 1 and 20 fluorine atoms or a $C_2$-$C_{20}$ group comprising between 1 and 20 fluorine atoms.

6. The compound according to claim 3, wherein the at least one antifouling moiety is a fluorinated substituted or unsubstituted aryl.

7. The compound according to claim 1, wherein the at least one antifouling moiety comprises one or more fluorinated amino acids.

8. The compound according to claim 7, wherein the fluorinated amino acid is a fluorinated phenylalanine derivative, wherein the fluorine atom substitutes one or more phenyl ring positions.

9. The compound according to claim 8, wherein the fluorinated phenylalanine derivative is selected from o-fluorophenylalanine, m-fluorophenylalanine and p-fluorophenylalanine.

10. The compound according to claim 1, wherein the at least one amino acid sequence promoting adherence of cells is RGD (Arg-Gly-Asp) or RGDS (Arg-Gly-Asp-Ser) (SEQ ID NO: 1).

11. The compound according to claim 1, wherein the compound is selected from the group consisting of J-X—Z, J-Z—X, X—Z-J, X-J-Z, Z—X-J and Z-J-X; wherein
   J is the at least one surface-adsorbing moiety,
   X is the at least one antifouling moiety,
   Z is the at least one amino acid sequence promoting adherence of cells; and
   each "-" designates a covalent bond or a linker moiety.

12. The compound according to claim 11, wherein the linker moiety is selected from substituted or unsubstituted carbon chains.

13. The compound according to claim 12, wherein the linker moiety is composed of two or more amino acids.

14. The compound according to claim 1, wherein the compound is of the general Formula (I):

J-X—Z      (I)

wherein
   J is the at least one surface-adsorbing moiety,
   X is the at least one antifouling moiety,
   Z is the at least one amino acid sequence promoting adherence of cells, and
   each "-" designates a covalent bond or a linker moiety.

15. The compound according to claim 1, wherein the compound is of general Formula (III):

$J_n$-$X_m$—$Z_k$      (III)

wherein
   J is the surface-adsorbing moiety,
   X is the antifouling moiety,
   Z is the amino acid sequence promoting adherence of cells, and
   each "-" designates a covalent bond or a linker moiety, and
   each of n, m and k, independently of the other, is an integer between 1 and 10.

16. The compound according to claim 15, wherein in the compound of Formula (III) n is 1, m is 2 and k is 1 and the compound is of Formula (IV):

J-X—X—Z      (IV)

wherein each of the two X groups are optionally the same.

17. The compound according to claim 1, wherein the compound is:
DOPA-Phe(4F)-Phe(4F)-Arg-Gly-Asp, designated Peptide 1 (SEQ ID NO: 14).

18. The compound according to claim 1, wherein the compound is a pentapeptide or a hexapeptide of the general Formula (V) or Formula (VI):

X—X-J-Z　　(V)

Z—X—X-J　　(VI)

wherein
J is the at least one surface-adsorbing moiety,
X is the antifouling moiety,
Z is the at least one amino acid sequence promoting adherence of cells; and
each "-" designates a covalent bond or a linker moiety, wherein each of the two X groups are optionally the same.

19. The compound according to claim 1, wherein the compound is selected from:

J-X—X—RGD　　(VII)

X—X-J-RGD　　(VIII)

RGD-X—X-J　　(IX)

(SEQ ID NO: 1) RGDS-X—X-J　　(X) and

X—X-J-RGDS (SEQ ID NO: 1)　　(XI), wherein
J is the at least one surface-adsorbing moiety,
X is the antifouling moiety; and
each "-" designates a covalent bond or a linker moiety, wherein each of the two X groups of the compound are optionally the same.

20. The compound according to claim 1, having the structure:

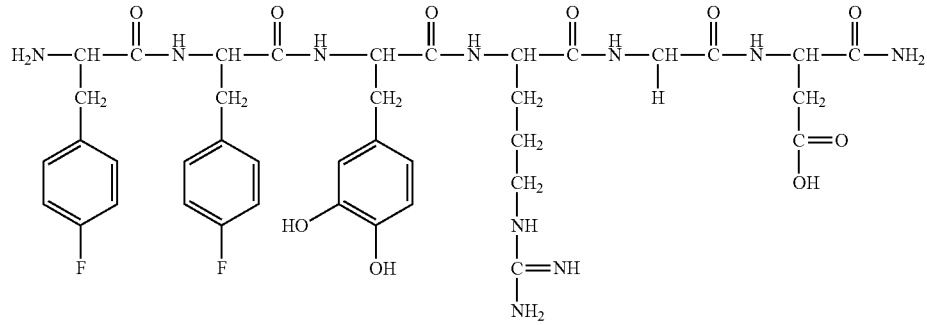 [SMILES: N=C(N)NCCCC(NC(=O)C(Cc1ccc(O)c(O)c1)NC(=O)C(Cc1ccc(F)cc1)NC(=O)C(N)Cc1ccc(F)cc1)C(=O)NCC(=O)NC(CC(=O)O)C(N)=O]

21. A medical device or implant comprising a film comprising at least one compound according to claim 1.

22. A method of anchoring or attracting cells onto a surface region of an implantable device or object, said method comprising forming on a surface region of the implantable device or object, a film of at least one compound according to claim 1 and implanting said device or object, wherein the film promotes anchoring or attachment of cells thereto.

23. The method according to claim 22, wherein the at least one antifouling moiety comprises between 1 and 20 fluorine atoms.

24. The compound according to claim 22, wherein the at least one amino acid sequence promoting adherence of cells is RGD (Arg-Gly-Asp) or RGDS (Arg-Gly-Asp-Ser) (SEQ ID NO: 1).

25. A method of reducing biofouling caused by an organism on an implant post-operatively, said method comprising forming on a surface region of the implant a film of at least one compound according to claim 1 and implanting said implant, wherein the film promotes anchoring or attachment of cells thereto.

26. The method according to claim 25, wherein the at least one antifouling moiety comprises between 1 and 20 fluorine atoms.

27. The compound according to claim 25, wherein the at least one amino acid sequence promoting adherence of cells is RGD (Arg-Gly-Asp) or RGDS (Arg-Gly-Asp-Ser) (SEQ ID NO: 1).

28. A method of attracting body cells to and reducing biofouling on an implant or attracting body cells to an implant, said method comprising forming a film of at least one compound according to claim 1 on a surface region of the implant and implanting said implant.

29. The method according to claim 28, wherein the at least one antifouling moiety comprises between 1 and 20 fluorine atoms.

30. The compound according to claim 28, wherein the at least one amino acid sequence promoting adherence of cells is RGD (Arg-Gly-Asp) or RGDS (Arg-Gly-Asp-Ser) (SEQ ID NO: 1).

31. A method for reducing biofouling of an implant having been placed in a body cavity or on a tissue, said method comprising the step of forming a film of at least one compound according to claim 1 on a surface region of an implant prior to implantation.

32. The method according to claim 31, wherein the at least one antifouling moiety comprises between 1 and 20 fluorine atoms.

33. The compound according to claim 31, wherein the at least one amino acid sequence promoting adherence of cells is RGD (Arg-Gly-Asp) or RGDS (Arg-Gly-Asp-Ser) (SEQ ID NO: 1).

34. A method for attracting body cells to an implant intended for implantation in a subject, said method comprising coating a surface region of the implant prior to implantation with a film comprising at least one compound according to claim 1.

35. The method according to claim 34, wherein the at least one antifouling moiety comprises between 1 and 20 fluorine atoms.

36. The compound according to claim 34, wherein the at least one amino acid sequence promoting adherence of cells is RGD (Arg-Gly-Asp) or RGDS (Arg-Gly-Asp-Ser) (SEQ ID NO: 1).

37. A method for attracting body cells to and reducing biofouling of an implant after implantation, the method comprising coating a surface region of the implant prior to implantation with at least one compound according to claim 1.

38. The method according to claim 37, wherein the at least one antifouling moiety comprises between 1 and 20 fluorine atoms.

39. The compound according to claim 37, wherein the at least one amino acid sequence promoting adherence of cells is RGD (Arg-Gly-Asp) or RGDS (Arg-Gly-Asp-Ser) (SEQ ID NO: 1).

* * * * *